(12) United States Patent
Morgan et al.

(10) Patent No.: US 7,306,592 B2
(45) Date of Patent: Dec. 11, 2007

(54) SYSTEM AND METHOD FOR REGULATING AN AMOUNT OF THERMAL ENERGY GENERATED BY AN ELECTROSURGICAL TOOL

(75) Inventors: Roy Morgan, San Jose, CA (US); Heber Saravia, San Francisco, CA (US); Jens Voges, Palo Alto, CA (US); Mani Prakash, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 10/228,298

(22) Filed: Aug. 26, 2002

(65) Prior Publication Data

US 2003/0004508 A1 Jan. 2, 2003

Related U.S. Application Data

(60) Division of application No. 09/799,817, filed on Mar. 5, 2001, now Pat. No. 6,461,352, which is a continuation-in-part of application No. 09/310,067, filed on May 11, 1999, now Pat. No. 6,214,003.

(51) Int. Cl.
*A61B 18/14* (2006.01)

(52) U.S. Cl. .............................. 606/32; 606/38; 606/41; 606/48; 606/50

(58) Field of Classification Search ............ 606/37–42, 606/45–52; 607/100, 102, 115, 116
See application file for complete search history.

(56) References Cited

U.S. PATENT DOCUMENTS 4,682,596 A 7/1987 Bales et al.

(Continued)

OTHER PUBLICATIONS

Dyonics EP-1® Handpiece Membrane Switch, 5 Photographs, Mar. 2000.

(Continued)

*Primary Examiner*—Lee S. Cohen
(74) *Attorney, Agent, or Firm*—Flynn, Theil, Boutell & Tanis, P.C.

(57) ABSTRACT

An bipolar electrosurgical tool (10) for cauterizing or ablating tissue. The tool has a nose cone (12) which serves as a handle. A conductive shaft (14) extends from the nose cone. A tip assembly (18) with an active electrode (20) is mounted to the shaft. A circuit board (78) is mounted in the nose cone. Conductive traces that forming contact pads (96, 102) are formed on the circuit board. A web (108) formed from a single piece of elastomeric material is seated over the opening in which the printed circuit board is mounted to seal the opening shut. Integrally formed with the web are buttons (116, 118) that are in registration over the contact pads. The buttons can be depressed downwardly towards the contact pads. When a button is so depressed, a conductive landing pad (120) integral with the button closes the connection between the traces that form the contact pad. Thus, the tool of this invention is provided with switches. The circuit board also has two conductive traces (92, 104a) that run in parallel. If there is a leak into the nose cone, a connection is established across these traces and shorts out a resistor (105). The shorting out of this resistor provides a control console (22) with an indication that there is a leak. The electrode is formed from a single piece of tantalum. The electrode has a head formed with a hole (172) trough which fluid flows. The electrode is seated in a sleeve (136*b*) provided with a through bore (177) in registration with the electrode hole.

21 Claims, 19 Drawing Sheets

U.S. PATENT DOCUMENTS

| | | |
|---|---|---|
| 4,932,952 A | 6/1990 | Wojciechowicz, Jr. |
| 5,217,478 A | 6/1993 | Rexroth |
| 5,334,193 A | 8/1994 | Nardella |
| 5,385,148 A * | 1/1995 | Lesh et al. .................. 600/471 |
| 5,683,366 A | 11/1997 | Eggers et al. |
| 5,697,281 A | 12/1997 | Eggers et al. |
| 5,697,882 A | 12/1997 | Eggers et al. |
| 5,697,909 A | 12/1997 | Eggers et al. |
| 5,712,543 A | 1/1998 | Sjostrom |
| 5,730,742 A | 3/1998 | Wojciechowicz |
| 5,807,393 A * | 9/1998 | Williamson et al. .......... 606/32 |
| 5,810,764 A | 9/1998 | Eggers et al. |
| 5,843,019 A | 12/1998 | Eggers et al. |
| 5,902,251 A * | 5/1999 | vanHooydonk ............. 600/549 |
| 5,902,272 A | 5/1999 | Eggers et al. |
| 5,954,716 A * | 9/1999 | Sharkey et al. ................ 606/32 |
| 6,053,912 A | 4/2000 | Panescu et al. |
| 6,224,592 B1 | 5/2001 | Eggers et al. |
| 6,238,391 B1 | 5/2001 | Olsen et al. |
| 6,383,177 B1 * | 5/2002 | Balle-Petersen et al. ....... 606/9 |

OTHER PUBLICATIONS

Linvatec Handpiece Membrane Switch, 3 photographs, Mar. 2000.

* cited by examiner

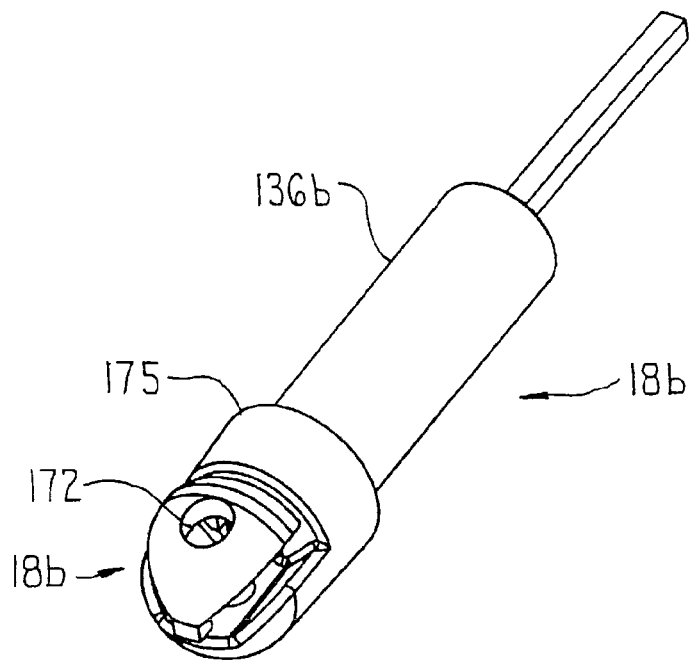
FIG. 18
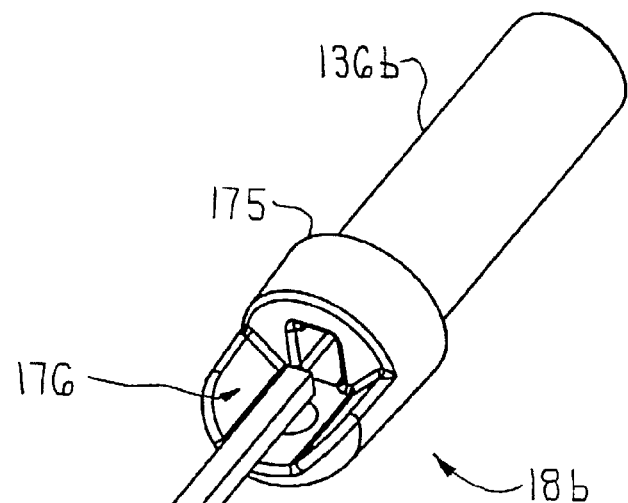
FIG. 19
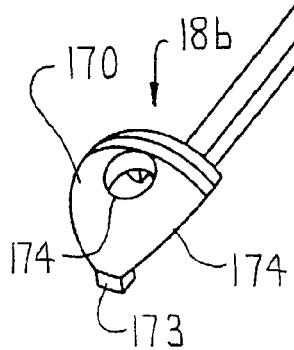

SYSTEM AND METHOD FOR REGULATING AN AMOUNT OF THERMAL ENERGY GENERATED BY AN ELECTROSURGICAL TOOL

RELATIONSHIP TO EARLIER FILED APPLICATION

This Application is a division of U.S. patent application Ser. No. 09/799,817, filed Mar. 5, 2001, now U.S. Pat. No. 6,461,352, which is a continuation-in-part of U.S. patent application Ser. No. 09/310,067, filed May 11, 1999, now U.S. Pat. No. 6,214,003. The foregoing applications are incorporated herein by reference.

FIELD OF THE INVENTION

This invention is related generally to a power-actuated surgical tool with a handle-mounted self-sealing switch assembly. One particular version of this tool is an electrosurgical tool that has handle-mounted switches, is relatively easy to manufacture, provides an indication if fluid penetrates its handle and that has tip that fosters fluid circulation adjacent the surgical site to which it is applied.

This invention is also related generally to a system and method of shrinking capsulary tissue and, more particularly, to a system and method for shrinking capsulary tissue by applying heat, thermal energy, to the tissue.

BACKGROUND OF THE INVENTION

Electrosurgical tools have been used for a number of years to cut and shape tissue at the surgical sites to which these tools are applied. A typical electrosurgical tool has an elongated shaft, sometimes called a "probe," with a handle at one end and a tip at the opposed end. One type of electrode surgical tool available to surgeons is referred to as a bipolar electrosurgical tool. An active electrode is fitted into the tip of this tool. The shaft of the bipolar electrosurgical tool functions as the return or reference electrode. The tool is applied to a surgical site at which there is a saline solution, a conductive fluid. A voltage is applied at a very high frequency, 50 k Hz to 10 M Hz, from the active electrode to the adjacent end of the shaft. This signal flows through, arcs through, the saline solution and the body tissue against which the tip is applied. When the signal is at a relatively low power, typically under 40 Watts, the signal can coagulate fluid such as blood to seal the tissue closed. When the signal is at a relatively high power, typically 20 Watts or more, it vaporizes the tissue to which it is applied so as to ablate, remove, the tissue. The overlap in the power ranges between the coagulation and ablation modes of operation is due to the fact that, for a given power setting, whether or not a particular electrode coagulates or ablates tissue is also a factor of the size and shape of the head of the electrode. Often, when an electrosurgical tool is used to ablate tissue, it is considered to be operated in the "cutting" mode.

Many currently available electrosurgical tools are designed so that mounted to the handles are switches for regulating the on/off state of the tool and the mode in which the tool is operated. The mounting of these switches to the tool handle makes it possible for the surgeon to, with a single hand, control both the position of the tool and the operation of the tool. The switches are typically mounted to the tool handle in liquid-tight seal assemblies. This mounting is necessary to prevent the conductive liquid that is often present in a surgical environment from entering the handle and shorting out any electrical components therein.

Presently available electrosurgical tools work reasonably well for the purposes for which they are designed. However, there are still some limitations associated with the currently available tools. Some of these limitations are due to the fact that, when an electrosurgical tool is operated in the ablation mode, bubbles form on the surface of the active electrode. One reason these bubbles form is that the electrical energy discharged by the electrode heats the conductive saline solution that surrounds the electrode. The heating of this solution causes it to vaporize and form bubbles. Initially, when relatively low levels of heat are present, the fluid immediately adjacent the surface of the electrode is subjected to thin film boiling and transitional boiling. In this type of vaporization, relatively small bubbles of gaseous state solution form.

However, when additional thermal or electromagnetic energy is radiated from the surface of the active electrode, the adjacent saline solution is subjected to rapid nucleate boiling. During nucleate boiling, relatively large bubbles of vaporized solution form on the surface of the electrode. These bubbles are sometimes referred to as gas pockets. Moreover, during some high powered cutting modes of operation, the electrical current applied to the solution and surrounding tissue causes electrochemical processes to occur in this tissue and liquid. These electrochemical processes produce gaseous state products that contribute the formation of large bubbles and the gas pockets.

At a minimum, these bubbles are a nuisance. The presence of these bubbles interferes with the surgeon's view of the surgical site. This is especially a problem when the electrosurgical tool is employed in an endoscopic surgical procedure. In an endoscopic procedure, the electrosurgical tool is applied to the surgical site through a small opening formed in the patient's body known as a portal. The surgeon views the surgical site through an endoscope that is directed to the surgical site through another portal. An advantage of an endoscopic surgical procedure in comparison to a conventional surgical procedure is that it requires less of the patient's body to be opened up in order to gain access to the surgical site. However, when a conventional electrosurgical tool is employed in an endoscopic surgical procedure, the bubbles generated in the relatively small confines of the space of the surgical site can significantly block the surgeon's view of the site.

Moreover, these bubbles are electrically and thermally insulating. The large bubbles that form gas pockets during high powered cutting can inhibit the flow of new solution that rewets the electrode. Consequently, the bubbles reduce the extent to which current can arc through the tissue that is to be ablated. Sometimes, these bubbles significantly reduce current flow through the tissue. The current flow stays in the reduced state until the bubbles collapse or move away and the saline solution or body fluid flows back into the space between the electrode and the shaft. Thus, sometimes when a presently available electrosurgical tool is actuated, the current only flows in a pulse pattern through the tissue to be ablated.

Moreover, many current electrosurgical tools are provided with wire wound electrodes. It is difficult to form wire wound electrodes so that they have heads with shapes that are especially useful for performing electrosurgical procedures.

Providing a seal around the handle switches can significantly add to the overall cost and assembly of the tool.

Also, sometimes, even with the best seals, there may be liquid leakage into the handle of an electrosurgical tool. This leakage, if not promptly detected, at a minimum, can lead to the degradation of the tool performance. In a worse case scenario, this leakage can cause a conductive path to develop along the outer surface of the handle. If this occurs, the personnel handling the tool may be subjected to electrical shock.

Still another method by which an electrosurgical tool is employed to shape, remove very selected amounts of tissue is by a capsulary shrinkage procedure. In a capsulary shrinkage procedure, the cells forming soft tissue are desiccated, reduced in size. In this type of procedure, as a result of the heating of the active electrode, there is a conductive transfer of the heat from the electrode to the location at which the capsulary shrinkage of tissue is to occur. The thermal energy applied to the site causes the cells forming the tissue at the site to undergo capsulary shrinkage. This process is referred to as a thermally capsulary shrinkage procedure.

In a presently available electrosurgical tool, internal to the tip or distal end of the shaft there may be a small thermistor or other temperature-sensitive transducer. This transducer monitors the temperature of the active electrode to inferentially provide an indication of the temperature of the surgical site. This temperature data is very important because there is a limited temperature range to which tissue can be heated in order to foster its shrinkage without causing damage to the tissue. More particularly thermal capsulary shrinkage of tissue is best performed by heating the tissue to a temperature between 60 and 70° C. If the tissue is heated to a temperature above this range, it may suffer damage. More particularly, the cells forming the tissue may die if heated to a temperature above 70° C. Therefore, when a thermal capsulary procedure is now performed, the temperature of the active electrode is monitored in order to regulate the application of an energization voltage to the electrode. Specifically, the application of the energization voltage to the active electrode is controlled to maintain its temperature within the range at which the thermal capsulary shrinkage process can best occur and to prevent it from rising to level at which cell death or damage can occur.

One disadvantage of the presently available electrosurgical tools is that the transducer internal to the tool only measures the temperature of the adjacent active electrode. This temperature measurement is only an approximate measurement of the temperature at the site to which the electrode is applied. Given the presence of fluids and other material around the active electrode and, more particularly, between the transducer and the surgical site, this measurement may not accurately represent the temperature at the site to which the electrode is applied.

Still another disadvantage associated with the currently available electrosurgical tool relates to the fact that often an AC signal is used to energize the active electrode. This signal generates stray electromagnetic waves. These electromagnetic waves interfere with the generation of the output signal generated by the transducer. Accordingly, it is now common practice to energize an electrosurgical tool in an on/off/on/off pulsed pattern. During time periods when the energization signal is pulsed on, the transducer signal is not employed as a feedback signal since it is adversely affected by the stray electromagnetic waves. Only during the time periods at which the energization signal is pulsed off, and the transducer signal is relatively noise free, is the signal then employed by the downline components as the input signal for regulating the application of energy to the active electrode.

One disadvantage of this mechanism is that the pulsing of current through the active electrode may stress the material from which the electrode is formed. Another disadvantage of this process is that the pulsing causes the thermal energy generated by the electrode to itself be generated in an on/off/on/off pattern. The cyclic generation of this heat can cause it to be unevenly applied to the surgical site. The uneven application of this heat can in turn both make it difficult to control the application of heat and lengthen the time it takes to perform the desired thermal capsulary shrinkage procedure.

SUMMARY OF THE INVENTION

This invention is related generally to a new and useful electrosurgical tool. The tool of this invention has a tip assembly with an electrode that facilitates the flow of conductive fluid to constantly rewet the active electrode during low powered operation as well as the eduction of large bubbles/gas pockets away from electrode during higher powered operation. More specifically, the tip assembly is designed to foster convective fluid circulation around the surfaces of the electrode that constantly rewets those surfaces and transports the larger bubbles away from the electrode. This circulation also serves to clean debris away from the electrode. In order to foster this fluid flow, the electrode and a complementary insulator of the tip assembly of this invention are formed with portals through which this fluid flows.

The tool of this invention also has a handle, a nose cone, in which the circuitry internal to the tool is mounted on a printed circuit board. A leak detect circuit is located on the periphery of the printed circuit board. A complementary control console continually monitors the signal from this leak detect circuit. The switches integral with the nose cone include static components that are mounted on the printed circuit board. The switches have moving components that are integrally formed on a web that is fitted to the nose cone. The web is designed to self-seal into place when mounted to the nose cone.

In some versions, the tool of this invention also has a fiber optic cable that is fitted in the tool shaft and that extends proximally away from the tip. The fiber optic cable terminates at a transducer that is sensitive to infra-red light. The transducer, based on the quantity of the received light, generates an electrical signal representative of the temperature at the surgical site. The output signal generated by the transducer is applied to the control unit that regulates the application of the output power signal to the tool electrodes. The control unit uses the transducer output signal as a feedback signal for regulating the magnitude of the energization signal applied to the electrodes.

BRIEF DESCRIPTION OF THE DRAWINGS

This invention is pointed out with particularity in the claims. The above and further features of this invention may be better understood by reference to the following description taken in conjunction with the following drawings in which:

FIG. 18 is a perspective view of a second preferred tip assembly of this invention;

FIG. 19 is a partially exploded view of the second tip assembly in which the head of the electrode is upwardly directed;

DETAILED DESCRIPTION

Figure 1:
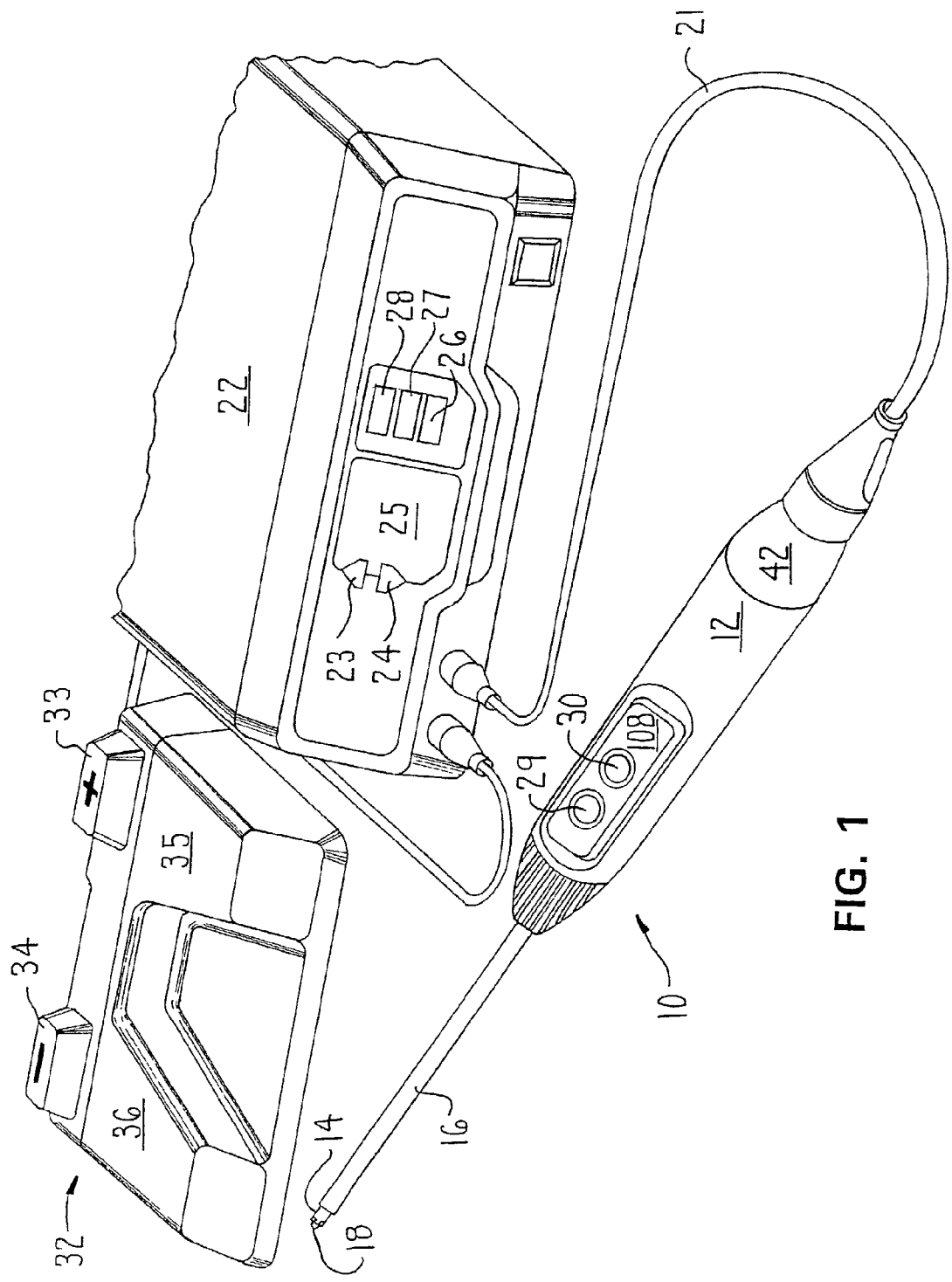
FIG. 1 is perspective view of an electrosurgical tool of this invention and the control unit and foot switch assembly to which the tool is connected.
Figure 2:
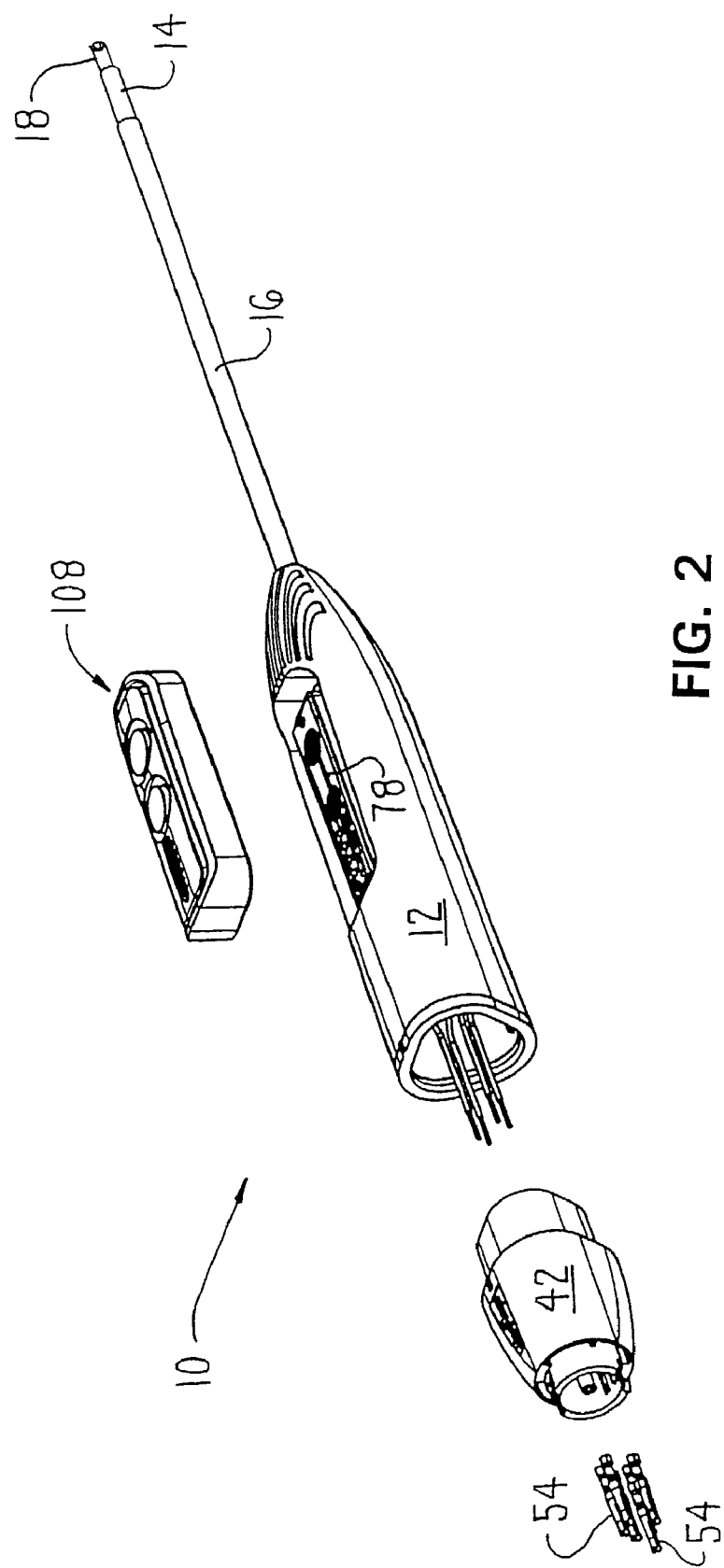
FIG. 2 is an exploded view of the electrosurgical tool.

FIGS. 1 and 2 depict the basic electrosurgical tool 10 of this invention. The tool 10 includes an elongated shell-like nose cone 12 that serves as the handle for the tool. Extending forward from the front end of the nose cone 12 is a shaft 14 formed from conductive metal. (In this application, "front", "forward" and "distal" shall be understood to mean towards the surgical site to which the tool is applied. "Rear", "rearwardly" and "proximal" shall be understood to mean away from the surgical site.) Substantially all of the shaft 14, except for its distal end, is covered by an insulating tube 16.

A tip assembly 18 extends forward from the distal end of shaft 14. An electrode 20 is housed in the tip assembly 18. More precisely, electrode 20 is considered an active electrode and the exposed distal end of shaft 14 functions as a return or reference electrode. When the electrosurgical tool 10 is actuated, current flows from electrode 20 to the exposed end of shaft 14. The current either coagulates or ablates the tissue against which the tip assembly 18 is placed.

The current for energizing the electrosurgical tool comes from a control console 22. Current flows from console 22 to the tool 10 through a detachable cable 21. The control console 22 converts the line voltage into a high frequency signal suitable for applying across the tool electrode 20 and the shaft 14. Depending on the surgeon's commands, the control console 22 applies either a low power coagulation-causing signal to electrode 20 or a high powered, ablation-causing signal.

The actual power of the signal generated by the control console 22 is also a function of the type of electrosurgical tool that is attached to the console as will be discussed hereinafter. Also, the surgeon is capable of setting the power to a specific level. For example, based on the depression of either an up switch 23 or a down switch 24 on the face of the console 22 the surgeon can, respectively, raise and lower the power setting of the tool when the tool is operated in the cutting mode. A display 25 indicates the cutting mode power level at which the electrosurgical is set to operate. By depressing a low power button 26, a medium power button 27 or a high power button 28 on the face of the console, the surgeon can control which one-of-three power levels the tool is operated at when it is operated in the coagulation mode.

The actual on/off actuation of the electrosurgical tool is controlled by two normally-open switches 29 and 30 mounted to the nose cone 12. When the surgeon wants to operate the electrosurgical tool 10 in the cutting mode, he/she depresses switch 29. When the surgeon wants to operate the electrosurgical tool in the coagulation mode, he/she depresses switch 302

A surgeon may alternatively control the tool 10 with a foot switch assembly 32. Foot switch assembly 32 includes a set of depressible foot switches 33, 34, 35 and 36 that respectively, can be depressed to perform that same functions as are performed by up switch 23, down switch 24, cutting-on switch 29 and coagulation-on switch 30.

Figure 3:
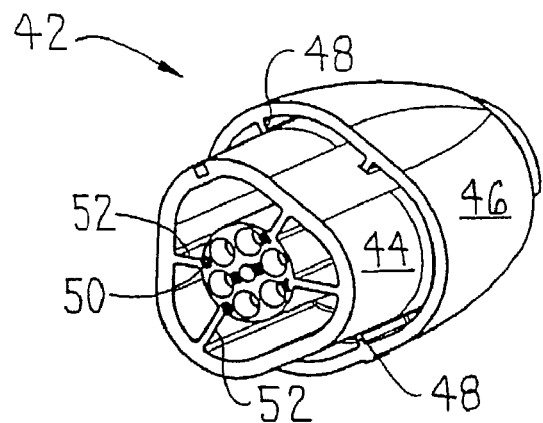
FIG. 3 is a perspective view of the hub.
Figure 4:
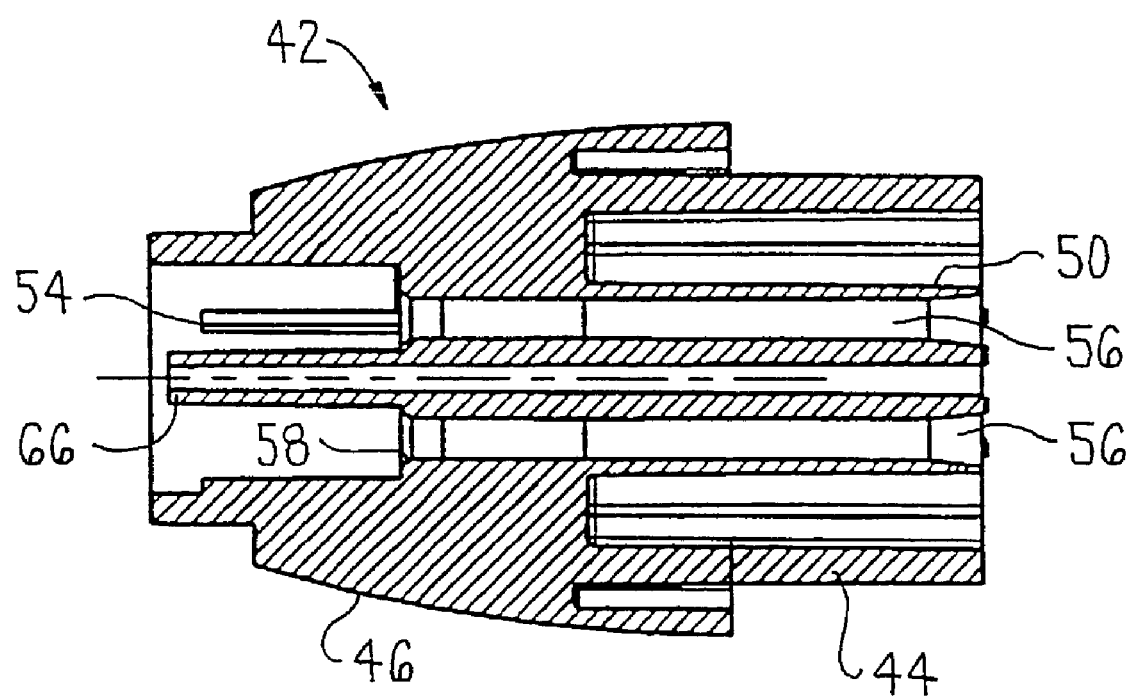
FIG. 4 is a cross sectional view of the hub.

The portion of the electrosurgical tool 10 to which the cable 21 is attached is a hub 42. The hub 42, which is the most rearwardly positioned portion of the tool 10 is formed from a plastic such as PVC or ABS. The hub 42, now described in detail by reference to FIGS. 3 and 4, is generally shaped to have a forward extending inner shell 44 that is seated inside the open rear end of the nose cone 12. An outer shell 46 is located around the exposed rear end of the inner shell 44. Small ribs 48 extend between the inner and outer shells 44 and 46, respectively, to provide stability to the outer shell. The outer shell 46 is the exposed portion of the hub 42. The hub 42 has a solid, cylindrical core 50 that extends from the end of the hub forward axially through the inner shell 44. Supports 52 that extend between the core 50 and inner shell 44 hold the core in position.

Figure 5:
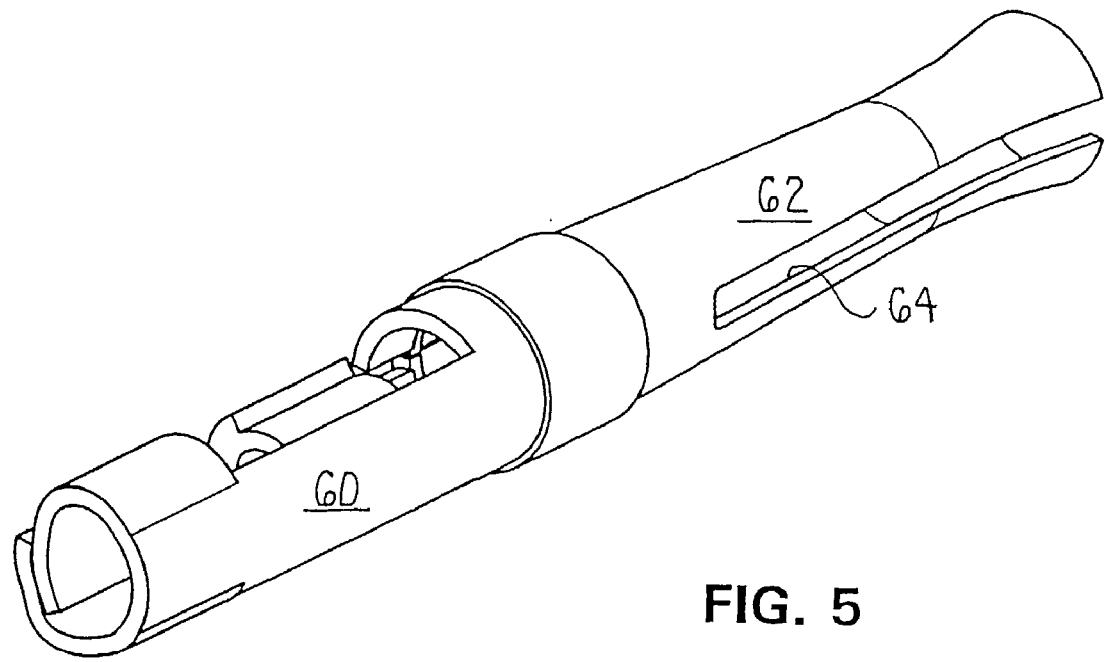
FIG. 5 is a perspective view of one of the connector pins that is mounted to the hub.

Socket pins 54 seated in the core 50 receive pins integral with the cable 21, (cable pins not illustrated). Each socket pin 54 is seated in a separate through bore 56 that extends through the core 50 along an axis that is parallel to the longitudinal axis of the bore. The core 50 is formed so that the rear end of each bore 56 has an outwardly chamfered section 58. This shaping of the bores 56 facilitates the insertion of the socket pins 54 into the bores. From FIG. 5 it can be seen that each socket pin 54 has first and second sections 60 and 62, respectively. Each first section 60 is generally sleeve shaped and is designed to receive a wire that is crimped in place. The pin first section 60 is the portion of the pin 54 seated in the bore 56. The pin second section 62 is sleeve like and further formed to have a slit 64 that runs approximately the length of the section. The pin second section is the portion of the pin that extends rearwardly out of the hub core 50. The second section 62 is the portion of the pin that receives the complementary pin integral with cable 21. One suitable socket pin 54 is manufactured by AMP, Inc. of Harrisburg, Pa.

It will be further noted that, in the depicted version of the invention, a small post 66 is integrally formed with the core 50 and extends rearwardly from the end of the core. Post 66 prevents the socket pins 54 from being inadvertently bent.

Figure 6:
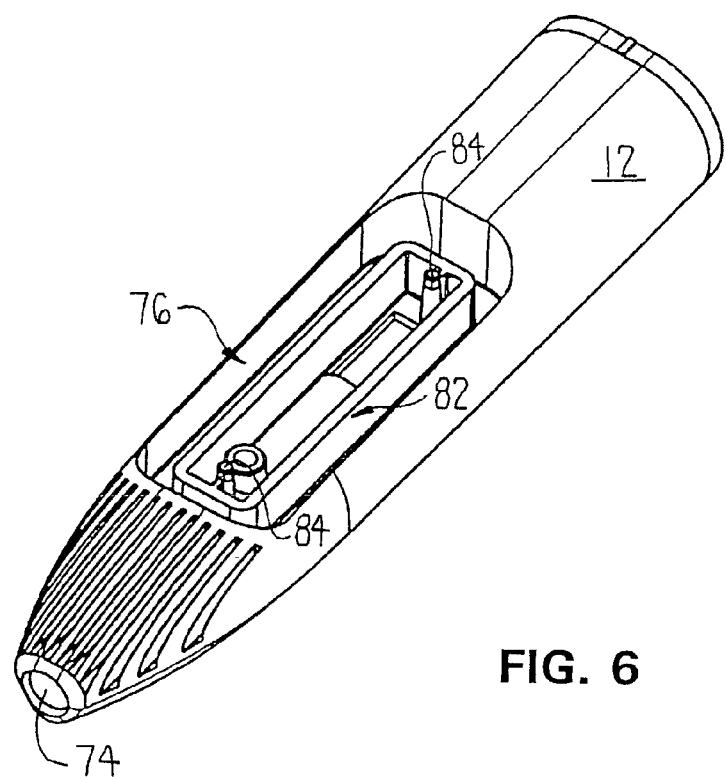
FIG. 6 is a perspective view of the nose cone of the electrosurgical tool.
Figure 7:
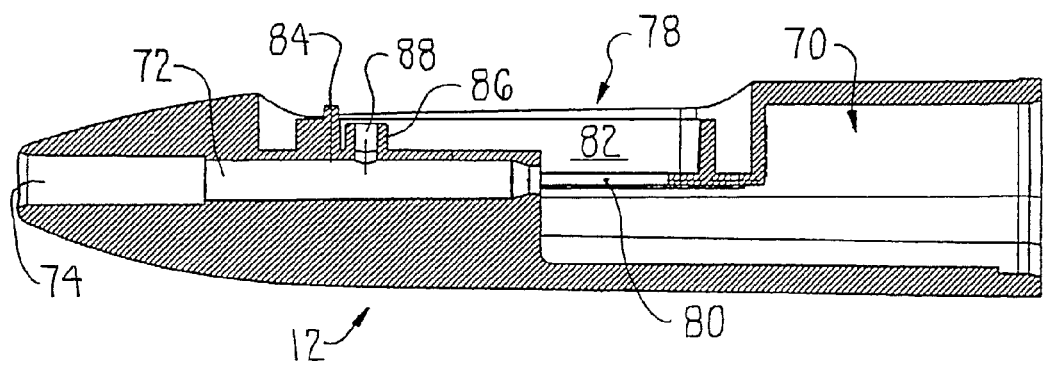
FIG. 7 is a cross sectional view of the nose cone.

The nose cone 12, now described by reference to FIGS. 6 and 7, is formed from a plastic such as PVC or ABS. The nose cone 12 has a generally elongated shape. The front end of the nose cone 12 is shaped to have an inwardly directed taper. Shaft 14 and insulating tube 16 extend out of the front end of the nose cone 12. The front end of the nose cone 12 is generally solid. Nose cone 12 is further formed to have a void space 70 that extends from approximately the longitudinal mid point of the nose cone to the open rear end of the nose cone. The hub inner shell 44 seats extends into the open rear end of the nose cone 12 and seats in the adjacent portion of void space 70.

Nose cone 12 is further formed to have a bore 72 that extends rearwardly from the front tip of the nose cone. Bore 72 extends rearwardly from the front of the nose cone into void space 70. The bore 72 is the space within the nose cone 12 in which the rear end of shaft 14 is seated. In the depicted version of the invention, nose cone 12 is formed so that the forward portion of bore 72 is actually a counterbore 74 that has a diameter that is slightly wider than that of the remaining, rearwardly extending portion of the bore. Counterbore 74 is provided to provide a space inside the nose cone for accommodating the rearward section of the insulating tube 16 this fitted around shaft 14.

The nose cone 12 is further formed to have an opening in the top of the cone that serves as a wiring space 76. The wiring space 76 is the space inside the nose cone in which a printed circuit board 78 (FIG. 2) is mounted. The wiring space 76 extends from a point rearward and above counterbore 74 to a point over void space 70. A passageway 80 connects the wiring space 76 to void space 70. Wires 79 from the printed circuit board 78 extend through passageway 80 so that they can be connected to the socket pins 54 integral with hub 42. The nose cone is also shaped to have a flange 82 that extends upwardly from the base of wiring space 76. The flange 82 is in the form of a closed-loop that is generally rectangularly shaped and that has rounded corners. Flange 82 serves as the member internal to nose cone 12 for supporting the printed circuit board 78. There are two opposed posts 84 located immediately inside the front and rear ends of the flange 82. Posts 84, which extend a slight distance above the top edge of flange 82, serves as the structural elements to which the printed wiring board 78 is snap fitted.

In the depicted version of the invention, nose cone 12 is also formed to have a boss 86 that extends upwardly from the base of wiring space 76 and that is located immediately rearward of the forward wall of flange 82. Boss 86 is formed with a conduit 88 that extends from the top of the boss into bore 72. In some preferred methods of manufacturing the electrosurgical tool 10 of this invention, shaft 14 and sleeve 16 are fitted in place within bore 72 and counterbore 74. Then, an adhesive is injected into bore 72 and counterbore 76 through conduit 88. This adhesive at least partially fills bore 72 so as to secure the shaft 14 and sleeve 16 in place.

Figure 8:
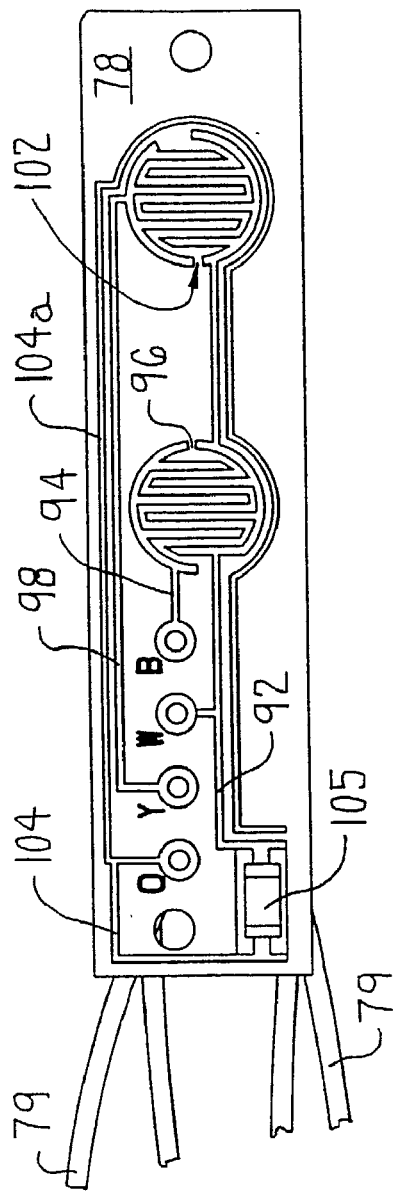
FIG. 8 is a plan view of a printed circuit board that is mounted inside the nose cone.

The printed circuit board 78, shown in detail in FIG. 8, is formed from any conventional substrate material from which printed circuit boards are formed. The top surface of the printed circuit board 78 is formed to have two conductive traces 92 and 94 that are arranged in one location to form a contact pad 96 for switch 30. A branch of conductive trace 92, in combination with a third conductive trace 98, are arranged at a second location on the printed circuit board to form a contact pad 102 for switch 29.

Figure 31:
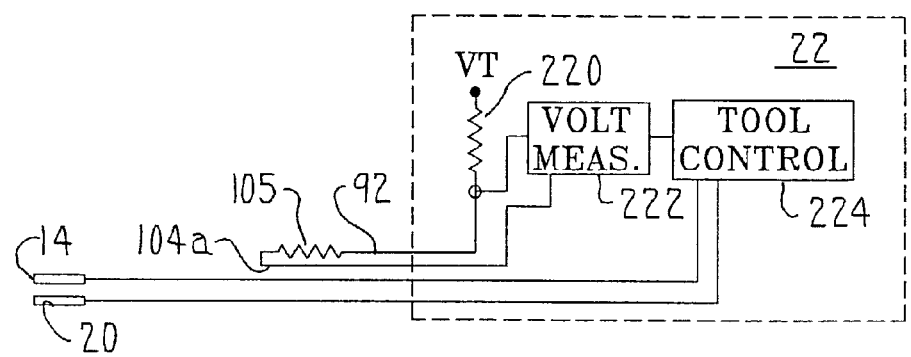
FIG. 31 is a block diagram depicting how the leak detect trace and complementary control console of the tool of this invention cooperate to prevent the actuation of the tool when a leak is detected in the handle.

Printed circuit board 78 also has a fourth conductive trace 104. A resistor 105 extends between trace 92 and trace 104. Resistor 105 serves as an identification member that identifies the particular type of electrosurgical tool. In one preferred version of the invention, when the tool 10 is connected to the control console 22, resistor 105 becomes part of a voltage divider 220 (FIG. 31), the rest of which is internal to the control console. A voltage measuring circuit 222 internal to the control console 22 measures the voltage across the resistor 22. This voltage indicates to the control console 22 the power levels of the signals that should be applied to the electrosurgical tool attached to the console. The console 22, based on this indication, applies an energization signal appropriate for the type of tool to the tool 10.

It will further be observed that conductive trace 104 is arranged on the printed circuit board 78 so that a branch 104*a* of the trace extends around the outer perimeter of the board. Conductive trace 104*a* is arranged so that it is in close proximity to the portions of conductive trace 92 that form contact pads 96 and 102. In particular, it will be observed that conductive trace 92 defines at least 90° of the perimeter of each contact pad 96 and 102. Trace 104*a* is parallel to the portions of the trace 92 that define the perimeter of the contact pads. More particularly trace 104*a* is spaced a maximum of 30 mils (0.030 inches) and preferably 20 mils or less away from the portions of trace 92 that define the perimeter of the contact pads 96 and 102. The purpose of this arrangement will be explained hereinafter.

Figure 11:
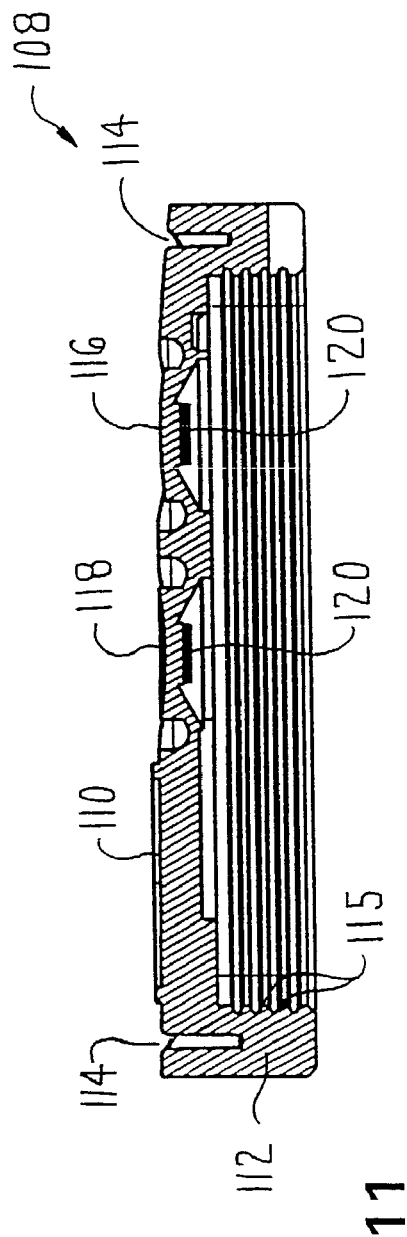
FIG. 11 is a cross sectional view of the web.
Figure 10:
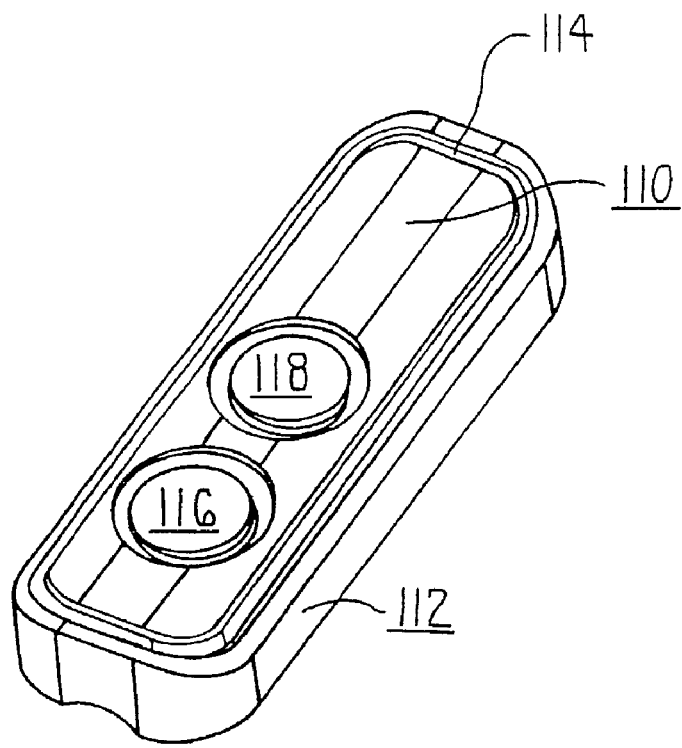
FIG. 10 is perspective view of the top of the web.

A web 108, seen in FIGS. 10 and 11, formed of elastomeric material such as silicon rubber covers the nose cone wiring space 76 and printed circuit board 78. The web 108 is shaped to have a generally flat base section 110 that substantially covers the wiring space 76. A lip 112 extends perpendicularly downwardly from the perimeter of base section 110 and surrounds the base section. The lip 112 is formed to have a slit 114 that is extends downwardly from a position located in the middle of the lip and that extends circumferentially around the web 108. The web 108 is further formed so that ribs 115 extend the inner wall of the lip 112.

Web 108 is dimensioned to be compression fitted into wiring space 76. Specifically, the lip 112 of web 108 is designed to tightly fit, compression secure, into the space between the outer wall of nose cone flange 82 and the walls internal to the nose cone 12 that define the outer perimeter of wiring space 76. When the web 108 is so fitted in place, the web ribs 115 collapse inwardly. When the web is so positioned, it also serves to hold the printed circuit board 78 in position.

The web 108 is further shaped to have two flexible buttons 116 and 118 that are integrally formed with base section 110. Button 116 is the moving component of switch 29 and is positioned over contact pad 102. Button 118 is the moving component of switch 30 and is positioned over contact pad 96. Each button 116 and 118 is formed so that the undersurface thereof, the surface facing the printed circuit board 78, functions as a landing pad 120. Each landing pad 120 is formed from graphite or other material to make the landing pad conductive. In some versions of the invention, the conductive material is a copper disk or copper paint that is applied to the underside of the button.

The depression of button 116 causes the associated landing pad 120 to abut and close the connection between conductive traces 92 and 98. The depression of button 118 causes the associated landing pad 120 to abut and close the connection between conductive traces 92 and 94.

Figure 12:
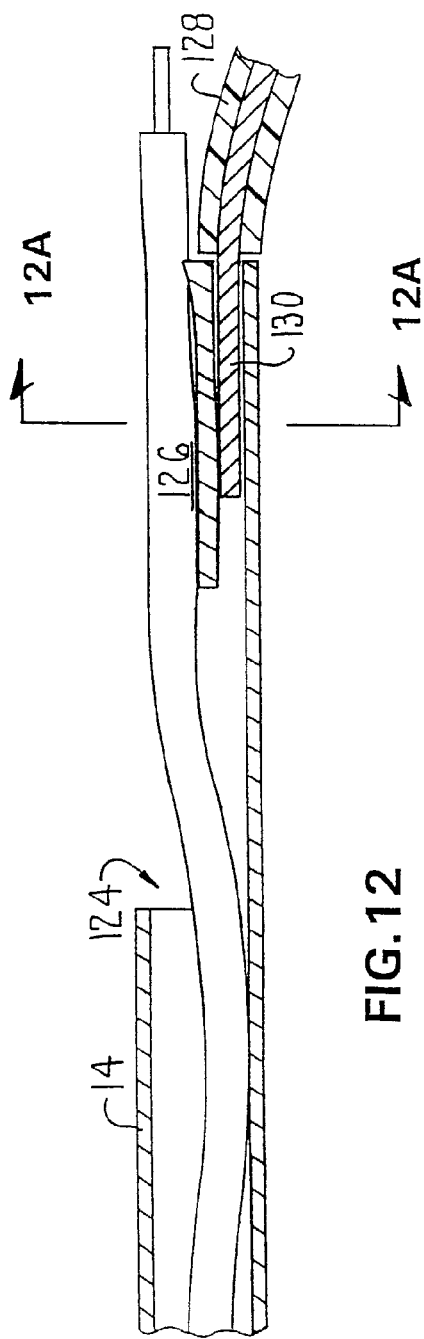
FIG. 12 is a cross sectional view of the proximal end of the shaft of the electrosurgical tool.

As seen by FIG. 12, the shaft 14 is generally in the form of an elongated hollow tube. Typically, the shaft 14 is formed from stainless steel. Shaft 14 is further formed so as to have a small window 124 that is located immediately forward of the proximal end of the shaft.

When the electrosurgical tool 10 of this invention is assembled, an insulated wire 126 through which current is supplied to electrode 20 is fed into the center of shaft 14 through window 124. An insulated wire 128 is employed to serve as the reference/return conductor from shaft 14. An exposed end 130 of wire 128 is placed in the proximal end of the shaft 14. The proximal end of the shaft 14 is then crimped down over the wire so as to mechanically and electrically connect wire 128 to the shaft. Typically, this crimping is performed by an automated tool with fingers that simultaneously presses different arcuate sections of the shaft inward towards the wire and against each other.

Figure 12A:
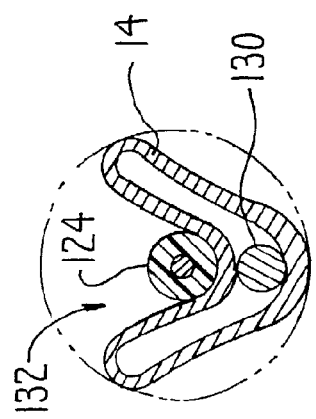
FIG. 12A is a cross sectional view of the proximal end of the shaft of FIG. 12.

As a result of this crimping, the crushed portions of the shaft 14 form an longitudinally extending slot 132, best seen in FIG. 12A. The portion of wire 126 that extends out of window 124 is seated in slot 132. It will further be observed that as a result of this crimping of the proximal end of shaft 14, the end of the shaft and as well as the section of wire 126 seated in slot 132, subtend a space less than the diameter of the rest of the shaft, (diameter shown in phantom in FIG. 12A). Thus, after this crimping operation, the crimped end of the shaft 14 can still be fitted in nose cone bore 72.

Figure 13:
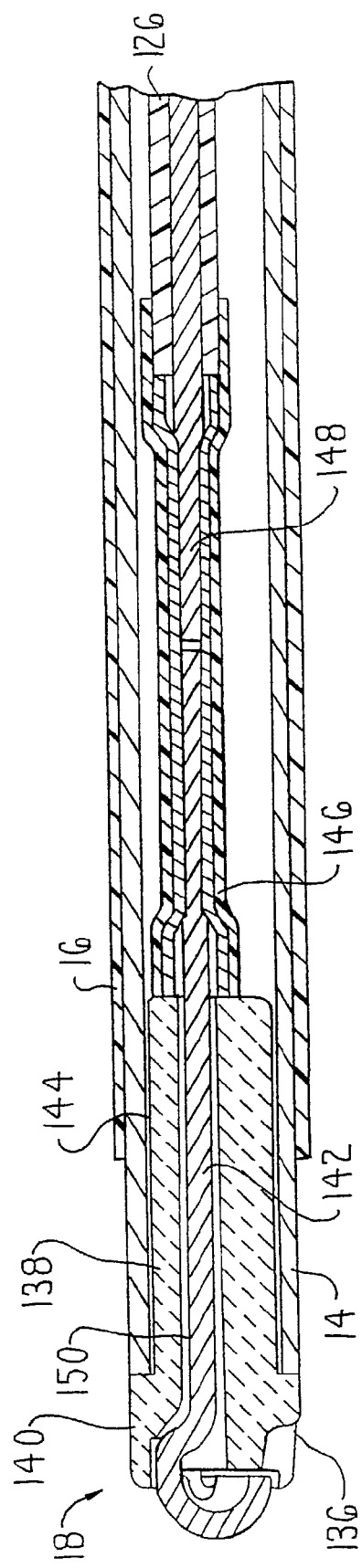
FIG. 13 is a cross sectional view depicting how the active electrode is held in place and secured to the complementary wire to which the electrode is connected.

FIG. 13 generically illustrates a tip 18 and electrode 20 of this invention, how these components are mounted in shaft 14 and how wire 126 is connected to the electrode 20. The tip 18 includes an insulating sleeve 136 formed from an appropriate material. In some versions of the invention, sleeve 136 is formed from a ceramic such as yttrium tetragonally stabilized zirconium oxide. The sleeve 136 has an elongated base 138 that is seated in the open distal end of shaft 14. Sleeve 136 is further formed to have a head 140, with a diameter equal to the outside diameter of shaft 14, which is integral with base 138. The sleeve head 140 abuts the open end of shaft 14. The exposed end of the electrode 20 seats in the sleeve head 140.

The active electrode 20 is typically formed from tantalum. Typically, the electrode 20 is formed out of single piece of metal that is molded into shape by a progressive die-stamping process. In some preferred versions of the invention, the active electrode 20 is formed from a sheet of metal having a thickness between 10 and 30 mils. In more preferred versions of the invention, the initial workpiece from which the electrode is formed has a thickness of between 15 and 25 mils. In the progressive die-stamping process, the metal workpiece from which the electrode 20 is formed is sequentially shaped in a set of dies until the electrode has the desired final end shape.

The material from which the preferred active electrode is formed, tantalum, is economically obtainable in sheet metal form and the metal itself can readily be stamped or molded into shape. Thus, by forming the electrode from tantalum, it is possible to provide electrodes having numerous different geometric shapes, some of which are disclosed below. Also, given ease with which it can be stamped or molded into shape, it is relatively economical to provide a specifically-shaped active electrode using the preferred material of this invention.

Electrode 20 is shaped to have an elongated stem 142. Stem 142 extends rearwardly through a longitudinally oriented bore 144 formed in the sleeve 136. The electrode stem 142 actually extends a short distance beyond the rear end of sleeve 136.

A crush tube 146 mechanically connects the exposed proximal end of electrode stem 142 to an exposed end 148 of wire 126. The crush tube 146 is formed from a malleable conductive metal such as stainless steel. During the manufacture of the tool 10, the electrode stem 142 is covered with an adhesive 150 and fitted in sleeve bore 144. Crush tube 146 is placed over the exposed end of the electrode stem 142 and the exposed end 148 of wire 126 is fitted in the distal open end of the crush tube. The crush tube 146 is then crimped down over the electrode stem 142 and wire end 148. In this last step, the exposed head end of the electrode 20 may be pushed rearward. Thus, the crush tube 146 serves multiple functions. While the adhesive 150 that holds the electrode stem 142 in sleeve bore 144 cures, the crush tube 146 serves as anchor to hold the electrode 20 in place. Even after the adhesive cures, the crush tube 146 holds the electrode 20 in the sleeve 136. Further, the crush tube 146 secures the electrode 20 to the wire 126 over which the energization current is supplied to the electrode.

Figure 14:
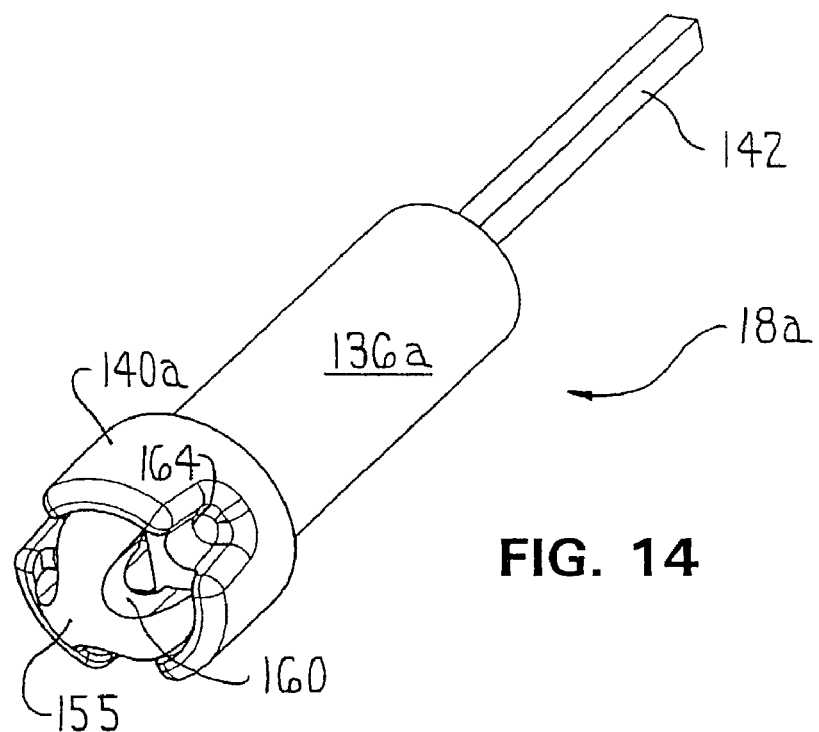
FIG. 14 is a perspective view of a first preferred tip assembly of this invention.
Figure 15:
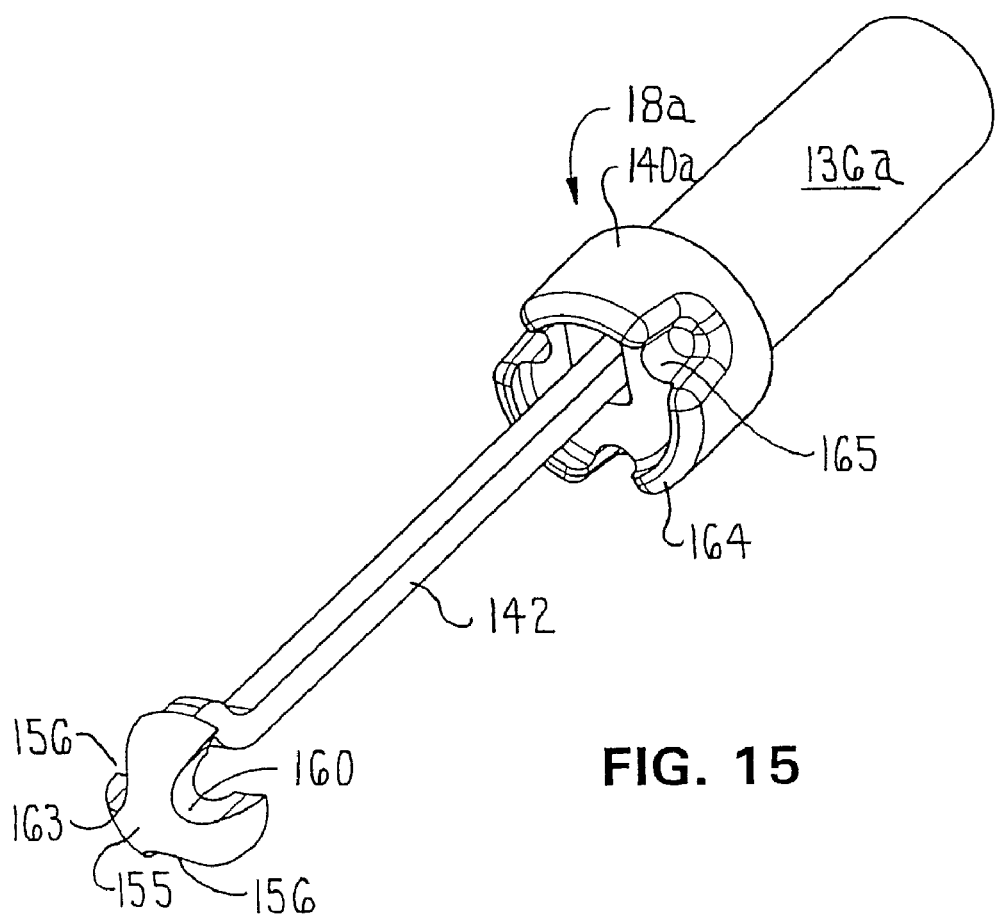
FIG. 15 is an exploded view of the first tip assembly.
Figure 16:
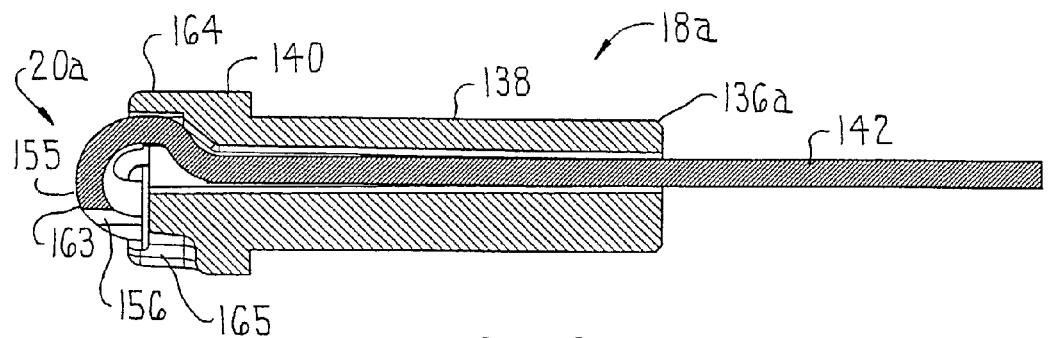
FIG. 16 is a cross sectional view of the first tip assembly.

The detailed structure of one particular tip assembly 18a that can be used with the electrosurgical tool 10 of this invention is now described by reference to FIGS. 14-16. Tip assembly 18a includes an electrode 20a seated in a complementary insulating sleeve 136a. Electrode 20a has a head 155 that extends from the distal end of electrode stem 142. The electrode 20a is shaped so that head 155 has the shape of a semi-spherical shell. Thus, the inner surface of the electrode is spaced away from the adjacent surface of the insulating sleeve 136a. It will be noted that the distal end of the electrode stem 142, the portion connected to the electrode head 155, is curved. More specifically, the distal end of the stem 142 is shaped so that the rest of the stem projects rearwardly along an axis that intersects both the center outer surface of the electrode head 155 and the center of the sphere inscribed by the head.

Electrode head 155 is formed to have three through windows 156. Windows 156 project upwardly from the outer perimeter of the head 155 and extend through the head. The windows 156 are spaced equangularly around the electrode head 20a. It will further be noted that electrode 20a is formed so that the windows 156 are defined by corners 163 that have a 90° profile around the outer surface of the electrode. Windows 156 subtend a significant amount of surface area on the outside of the electrode head 155. For example, if the outer surface of the electrode head subtends a radius of 67.5 mils, each window, which has a generally semicircular profile, subtends a radius of 20 mils. As a result of the formation of windows 156, the electrode head 155 has three curved side walls 160. The portions of the perimeter of the electrode head 155 between the windows 156 are referred to as the tines of the electrode head.

Sleeve 136a is formed with an open ended head 140a shaped to receive the head 155 of electrode 20a. The head 140a is formed to have a forward directed lip 164 that extends around the outer perimeter of the head. Lip 164 defines the space in the front end of the sleeve head 140a in which the electrode head 155 is seated. The lip 164 is formed with three equangularly spaced apart notches 165. When the electrode 20a is seated in sleeve 136a, the electrode windows 156 are in registration with the sleeve notches 165. Thus, the electrode windows 156 and sleeve notches 165 collectively form oval-shaped portals pathway that allow fluid to flow through the electrode head 155 from one side of the head 155 to the other side. The purpose for allowing this fluid flow is discussed below.

Figure 17A:
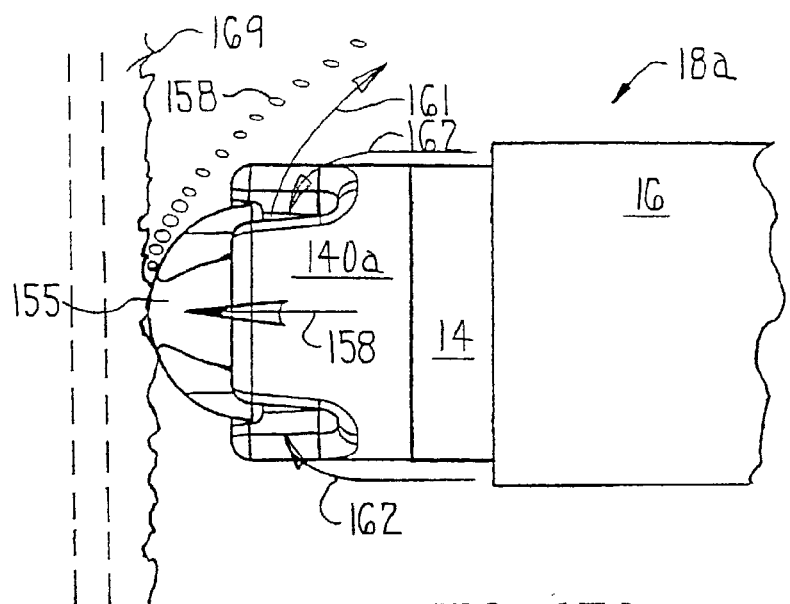
FIG. 17A is a side view of the flow of bubbles away from the first tip assembly when the tool to which it is attached is operated in the cutting mode.

Tip assembly 18a of this invention is designed to foster the flow of bubbles away from the surgical site to which the assembly is applied. FIG. 17A depicts the flow of bubbles 158 that occurs when the tip assembly 18a is initially applied to tissue 169 at a surgical site and the tool 10 is operated in the cutting mode. At this point in the surgical procedure, the tissue 169 is not yet bent outwardly by the force of the electrode head 155. At this point in the process, the following activities occur that foster bubble flow away from the surgical site. First, as a result of the current flow through electrode 20a, the electrode head 155 begins to heat up. The thermal energy in the electrode head heats the surrounding solution. The heating of this solution causes its expansion so that it becomes more buoyant than the surrounding solution. This buoyant solution convects switch away from the surgical site. Consequently cooler, less buoyant solution flows toward the surgical site as represented by arrow 158. Specifically, the replacement solution flows towards the outer surface of the electrode head since this is where some of this thermal expansion of solution is occurring.

However, the outer surface of the electrode head 155 is not the only location at which the heating causes the solution to convect away from tip assembly 18b. The solution adjacent the inner surface of electrode head 155 is also heated. This solution is similarly warmed to the point at which it likewise convects away from the from tip assembly 18a. More specifically, this solution convects away from the electrode head 155 through the portals defined by electrode head windows 156 and sleeve notches 165. This convective flow is represented by arrow 161. This convective flow away tip assembly 18a causes a portion of the replacement convective flow that is flowing towards the outer surface of the electrode head 155 to flow through the portals as represented by arrow 162. This fraction of the replacement flow replaces the heated fluid that is convected away from the inner surface of the electrode head 155. Thus the replacement solution flows towards the electrode head 155 along flow paths that run both parallel to the axis of the tool shaft and transverse to this axis. In other words, as a result of the heating of the solution adjacent the electrode head 155, a convective fluid flow pattern develops around the surgical site.

Eventually, sufficient thermal energy is supplied to the solution adjacent the surgical site that the solution vaporizes. This vaporization is the cause of the initial formation of bubbles at the surgical site. More particularly, this vaporization results in the rapid formation of bubbles 158 along both the inner and outer surfaces of the electrode head 155. These bubbles do not simply remain clustered around the electrode head 155. Instead, the convective flow away from the portals in the tip assembly educts the bubbles 158 in a stream that is directed rearwardly away from the electrode head 155.

The previously described convective flow of liquid towards the surgical site continues simultaneously with this bubble formation. The constant replenishment of this rewetting flow ensures that there is liquid-state fluid at the surgical site that is either thermally expanded, or being forced away from the site due to the rapid formation of bubbles. This liquid-state fluid flow further promotes the general migration of bubbles away from the surgical site.

Figure 17B:
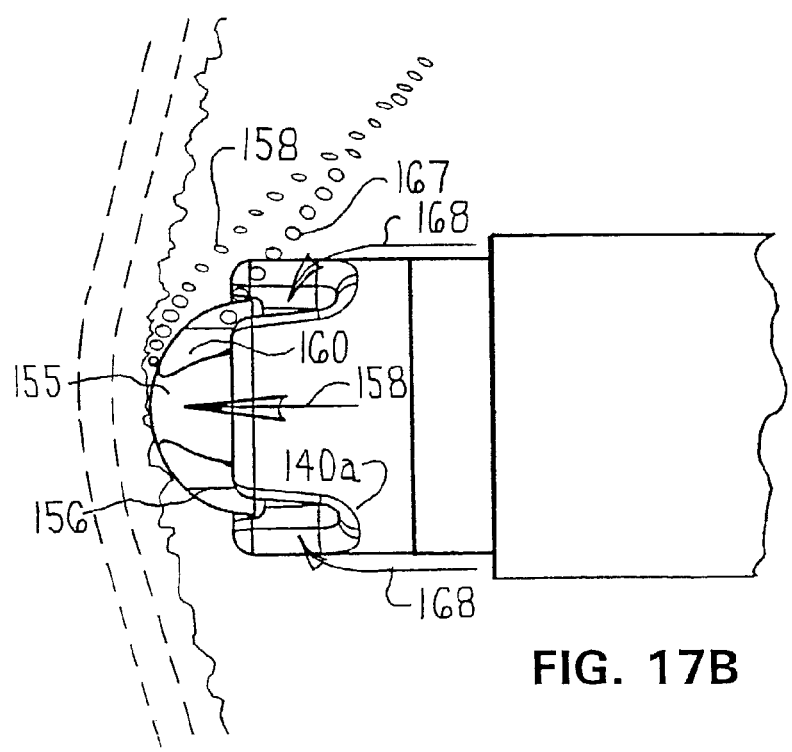
FIG. 17B is a side view of the flow of bubbles away from the first tip assembly after the tool to which it is attached has been in operation and the tissue to which the tip assembly is applied has flexed.
Figure 20:
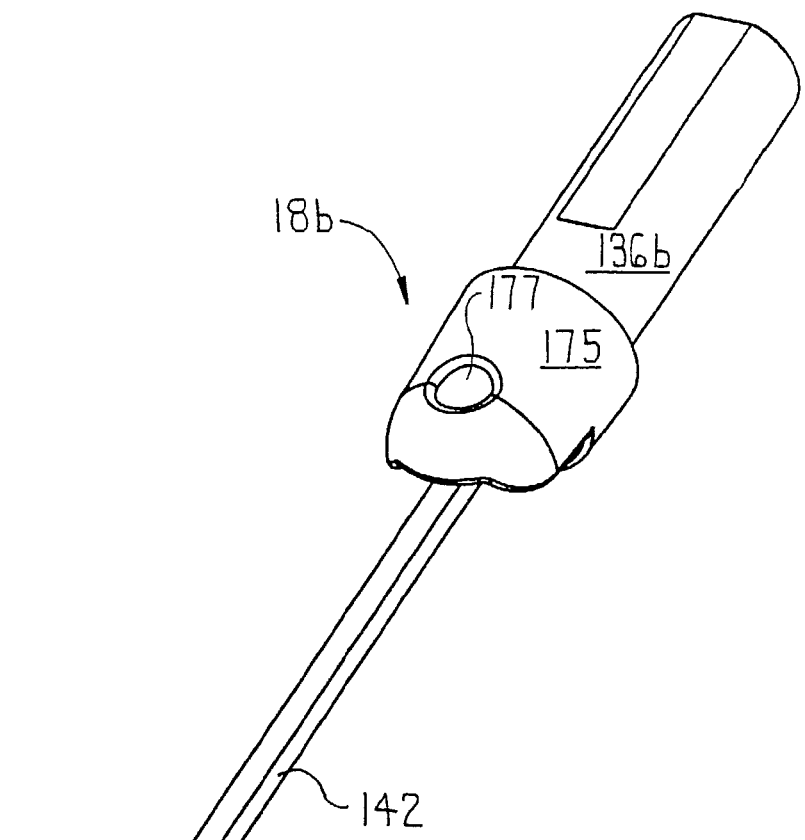
FIG. 20 is a partially exploded view of the second tip assembly in which the head of the insulating sleeve is upwardly directed.

As the surgical procedure continues, tip assembly 18a forces the adjacent tissue 169 to flex so as to develop the concave profile depicted in FIG. 17B. Eventually, bubbles 167 form adjacent the side walls 160 of the electrode head 155. It is believed these bubbles 167 form as a result of electrochemical reactions that take place due to the generation of relatively strong electromagnetic fields adjacent the electrode head 155. The concave bend of the adjacent tissue 169 directs the already existing convective fluid flow away from the tip assembly 18b rearwardly. Thus, these bubbles 167 tend to be caught up in this fluid flow and move rearwardly away from the surgical site. Moreover, it should be understood that bubbles 167 are able to move rearwardly because the portals through the tip assembly 18a provide a flow path for the replacement liquid that is flowing towards the electrode head. As discussed above, and as represented by arrow 168, this fluid is diverted laterally into the portals where it serves as replacement fluid for the solution that has been convected away from the inner surface of the electrode head 155. Furthermore, the bubbles 167 themselves serve to block the longitudinal flow of replacement fluid towards the outer surface of the electrode head 155. Since the portals provide a bleed flow path for this liquid-state fluid, this fluid does not function as a medium for transporting the bubbles forward towards the tissue 169 that defines the surgical site.

Furthermore, as previously discussed, the flow through some of the portals is bidirectional. This convective flow contributes to the eduction of the bubbles 167 away from the tip assembly 18a.

It will further be observed in FIG. 17B that vaporization induced bubbles 158 continue to be formed. These bubbles 158 become entrained in the flow of the bubbles produced adjacent the head side walls 160.

Thus, even when the tissue 169 against which the tip assembly 18a of this invention folds around the tip assembly, the bubbles formed as a result of the activation of the tool 10 do not simply become trapped around the tip. Instead, the fluid flow portals allow flow pathways to form. The bubbles are educted away from electrode head 155 through these pathways. Since the bubbles are continually forced away from the electrode head, replacement solution is able to continually flow towards the head so that the head is continually kept in contact with the solution, "rewetted." The constant rewetting of the electrode head 155 facilitates a relatively constant current flow, stable arcing, between the active electrode 18a and the shaft 14.

Moreover, the convective fluid flow away from the tip assembly 18b around the electrode head 155 prevents the bubbles that are formed adjacent the electrode head from becoming large in size. This is because, soon after a bubble is formed, it becomes trapped in the convective flow and is educted away from the electrode head 155. The constant eduction of newly formed bubbles away from the electrode head 155 prevents the bubbles that do form becoming large in size.

Figure 21:
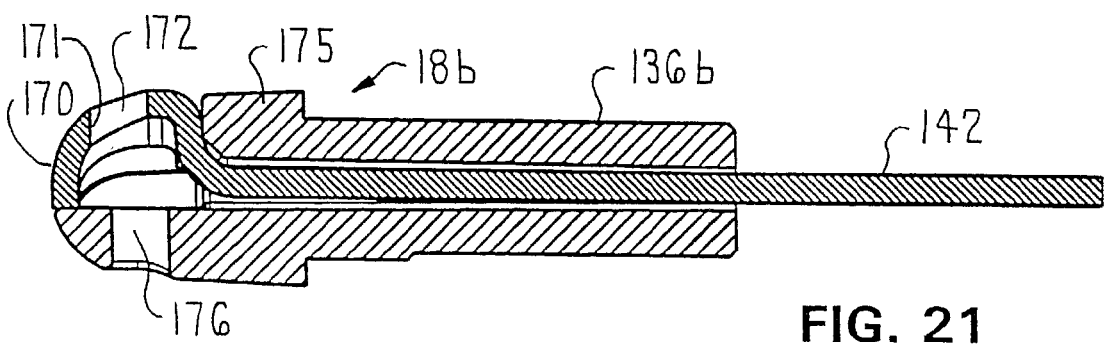
FIG. 21 is a cross sectional view of the second tip assembly.
Figure 22:
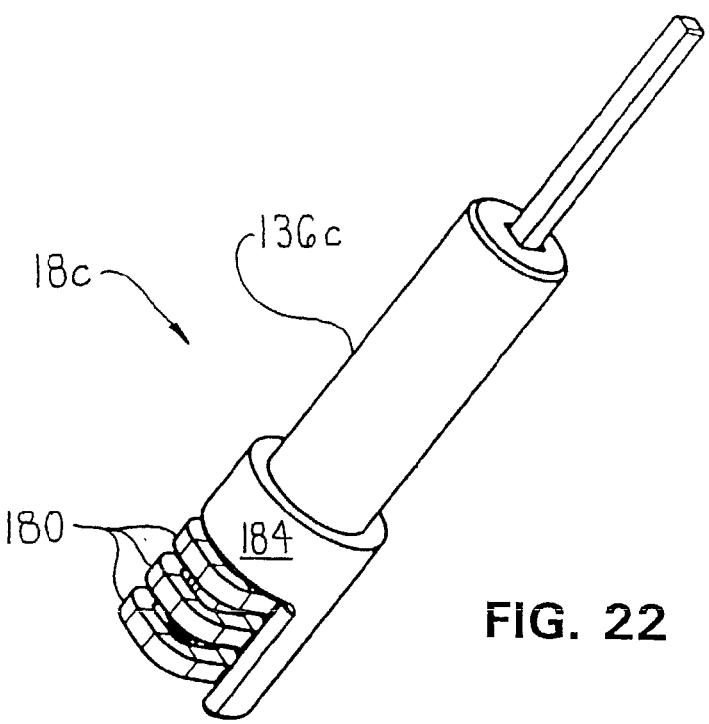
FIG. 22 is a perspective view of a third preferred tip assembly of this invention.
Figure 23:
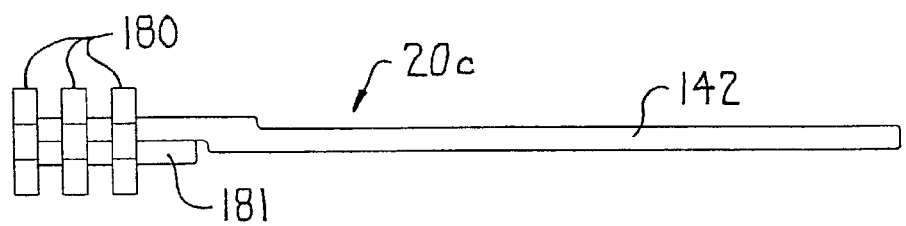
FIG. 23 is a plan view of the electrode of third tip assembly.
Figure 24:
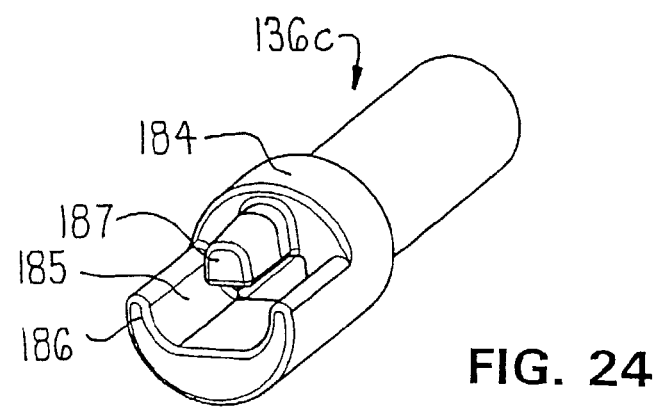
FIG. 24 is a perspective view of the insulating sleeve of the third tip assembly.
Figure 25:
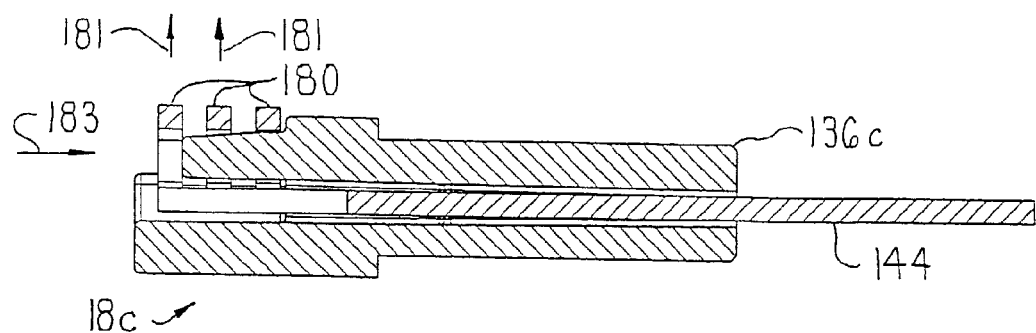
FIG. 25 is a cross sectional view of the third tip assembly.
Figure 26:
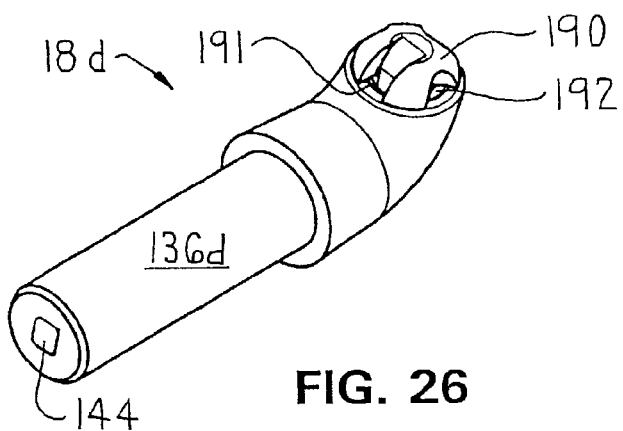
FIG. 26 is a perspective view of a fourth tip assembly of this invention.
Figure 27:
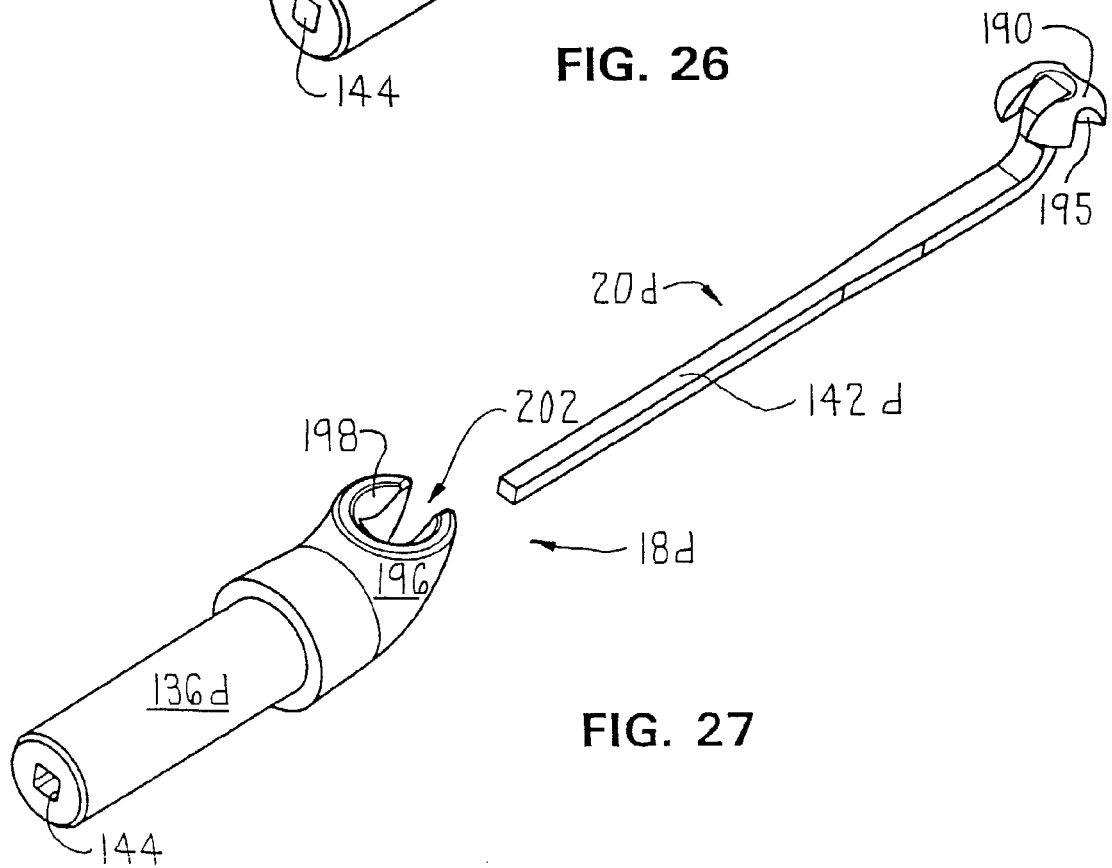
FIG. 27 is an exploded view of the fourth tip assembly.
Figure 28:
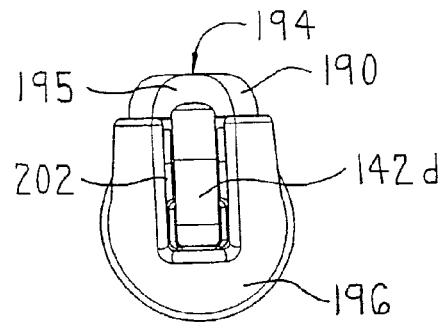
FIG. 28 front plan view of the fourth tip assembly.
Figure 29:
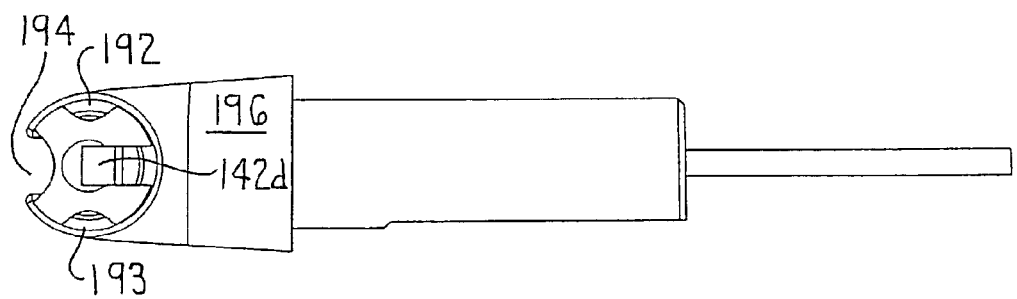
FIG. 29 is a top plan view of the fourth tip assembly.

A second tip assembly of this invention, tip assembly 18*b*, is now described by reference to FIGS. 18 and 21. Tip assembly 18*b* includes an electrode 20*b* with a head 170 that is generally in the shape of a one-eighth section of the shell of a sphere. Thus, the inner surface of the electrode head 170 is spaced away from the, adjacent surface of the insulator sleeve 136*b*. The electrode head 170 is further formed to have a small through portal 172. In some versions of the invention, head 170 inscribes a section of a sphere that has a radius of 67.5 mils, portal 172 has a radius of 20 mils. The electrode head is further formed with corners 174 that both define portal 172 and the side edges of the head. Corners 174 are defined by surfaces of the head 170 that meet at 90°. It will also be observed that electrode head 170 has side walls 171 that extend between the inner and outer surfaces of the electrode head. Two of the side walls 171 extend around the outer perimeter of the electrode head. A third side wall 171 defines portal 172.

Electrode 20*b* is further formed so that a nose 173, having a square cross section profile extends out from the distal tip of head 170. The purpose of nose 173 will be explained below.

Insulating sleeve 136*b* of tip assembly 18*b* has a head 175 with a generally cylindrically shaped profile. The distal end of head 172 is rounded. Head 175 is further formed to have a flow cavity 176 that extends into both the constant diameter main section and the distal end of the head. The sleeve head 175 is further formed to have a through bore 177 that extends laterally through the head from the outer surface of the head into the wall with in the head that defines the base of flow cavity 176. When tip assembly 18*b* is assembled, electrode 20*b* is seated in sleeve 136 so that the outer surface of the electrode head 170, in combination with the outer surface of the sleeve head 175 form the outer distal end of the tip assembly. When the tip assembly 18*b* is so assembled, the portal 172 formed in the electrode head 170 is in registration with the sleeve bore 177. Thus portal 172 and sleeve bore 177 form a contiguous flow pathway through which there is fluid circulation across the inner and outer surfaces of the electrode head 170.

Tip assembly 18*b* of this invention is used to contour or shape the tissue to which it is applied. When the tool 10 to which the tip assembly 18*b* attached is actuated, current flows between the electrode head 170 and the exposed end of the tool sleeve 14. When the electrode head 170 is pushed against the tissue to be ablated, nose 173 holds the side edges of the electrode head away from the adjacent surfaces of sleeve 136*b*. As a result of the heating of the solution adjacent the inner and outer surfaces of the electrode head 170, initially a convective flow of replacement solution flows towards across the electrode head through the contiguous flow pathway defined by electrode portal 172 and sleeve bore 177. As part of the convective flow pattern, the heated solution also flows out of the portal.

Eventually, bubbles develop adjacent the side walls 171 of the electrode head. These bubbles do not simply remain trapped within the tip and surrounding tissue. Instead, these bubbles become entrained in the portion of the convective fluid flow that moves away from the tip assembly 18*b* through the flow passageway. More particularly, it should be understood that since flow through the flow passageway is bidirectional along the length of the passageway, these bubbles will stream out of either the electrode head portal 172 or the sleeve bore 177.

The flow out of the flow passageway entrains bubbles that form around the outer side walls 171 of the electrode head 170 to flow with it. Thus, the bubbles that form along the side of the electrode head 170 are educted away from the head. This constant eduction of the bubbles serves to ensure that solution will continually flow towards the electrode head 170 so as to continually keep the head wetted.

FIGS. 22 through 25 illustrate a third tip assembly 18*c*. Tip assembly 18*c* includes an electrode 20*c* with three parallel, spaced apart tines 180 that are shaped to form loops. Electrode 20*c* is further formed to have small support bar 181 that extends perpendicularly across the ends of the tines that are spaced from stem 142. Once the metal forming the third electrode 20*c* is stamped out of a flat sheet of material, the tines 180 and the support bar 181 are wrapped around an anvil so that the support bar abuts against the distal end of the electrode stem 142. This wrapping of the metal provides the tines 180 with their loop shape.

Electrode 20*c* is seated in the head end of a sleeve 136*c*. The sleeve 136*c* is formed with a head 184 that has an outer diameter equal to the outer diameter of the adjacent shaft 14. The head is shaped so as to define in the distal two-thirds of the head a socket space 185 for receiving the distal end of electrode 20*c* including tines 180. More specifically, the head 184 is provided with side walls 186 so that approximately 200° of the outer circumference of each loop 180 is exposed, that is, can be placed in contact with tissue. The open end of the sleeve head 184, in combination with the void space in center of the loops and the interstitial spaces between the tines 180, serve as a portal and sub portals between the surfaces of tines and space outside the tip assembly 18*c*.

The sleeve head 184 is further shaped so as to project a small distance beyond the distal end of the most forward loop 180 of the electrode 20*c*. Sleeve head 184 is further formed to have a post 187 that extends forward from the wall of the sleeve that defines the rear end of socket space 185. When the electrode 20*c* is seated in the socket space 185, post 187 extends through the loops. When the tines 180 are pressed against the tissue, the post 187 provides mechanical support for the loops and prevents tissue from being caught in the tines.

The third electrode assembly 18*c* is used to remove large masses of tissue in areas that extend perpendicular to tool shaft 14. Assembly 18*c* is used by positioning the electrode 20*c* so that the exposed outer surfaces of the tines 180 are pressed against the tissue to be removed. When the electrosurgical tool 10 to which tip assembly 18*c* is attached is actuated, the solution surrounding the electrode tines 180 is heated. Cooler replacement solution flows towards the tines 180 from the open distal end of the sleeve head 184. This fluid flows through the tines 180 and around the sleeve post 187. The fluid then flows between the tines 180 so as to replace the fluid the heated fluid that convectively moves away from the tines. More particularly, as represented by arrows 181 in FIG. 25, the warmed fluid tends to flow away from the electrode 18*c* along flow paths that parallel to the planes in which the tines 180 are aligned. As represented by arrow 183, the replacement fluid flows towards the electrode along a flow path that is generally aligned with the center axis of the loops defined by the tines 180.

Eventually, bubbles start to rapidly form adjacent the surfaces of the tines 180. These bubbles become entrained in the convective fluid flow away from the tines 180. Thus, these bubbles do not simply become trapped between the tissue and the electrode where they can degrade the performance of the tool 10. Instead, these bubbles, as part of the circulation flow away from the electrode 20*c*, stream outwardly away from tip assembly 18*c*.

A fourth tip assembly of this invention, tip assembly 18*d*, is now described by reference to FIGS. 26-30. Tip assembly 18*d* includes an electrode 20*d* with a stem 142*d* shaped so that the distal end has a 90° curve. A head 190 is integrally formed with stem 142*d*. The electrode head 190 has a circular cross sectional profile. The lateral profile of the head 190 is that of a flattened semi-circle. The inner surface of the electrode head 190 is spaced away from the adjacent surface of the sleeve 136*d* against which the electrode head abuts. Four windows 191, 192, 193 and 194 are formed around the outer perimeter of head 190. Window 191 is formed by the void space from which the stem 142*d* extends. Windows 192 and 193 are located on either side of window 191 and are symmetric with respect to each other relative to that center axis through the head 190. Window 194 is located forward of window 191. Windows 191 is defined by straight edges. Windows 192-194 are defined by curved edges. The radius of curvature of the edges that define window 194 are greater than the radius of curvature of the edges that define windows 192 and 193. Electrode head 190, like the other electrode heads of this invention, is shaped so that the corners around the edges of the head and the windows 191-194 have 90° profiles.

It will also be observed that electrode head 190 has side walls 195 that define the perimeters of windows 191-194. The side walls extend between the inner and outer surfaces of the electrode head 190.

The sleeve 136*d* of the fourth tip assembly 18*d* is shaped so as to have a head 196 with a curved profile. Thus, the head has a face 198 that lies in a plane that is parallel to the longitudinal axis of the tool 10 with which tip assembly 18*d* is used. The head 196 is further shaped to have a notch 202 that extends rearward from the most distal end of the head. Notch 202 thus provides a fluid communication path that extends from the front end of sleeve head 196 to face 198.

When the electrode 20*d* is seated in the sleeve 136*d*, the distal end of the electrode stem 142*d*, the curved portion, seats in the rear end of the space defined by notch 202. The base surface of the electrode head 190 seats against the sleeve face 198. The inner surface of the electrode head 190 is spaced above the adjacent face 198 of the sleeve 136*d*. When the tip assembly 20*d* is so assembled, window 194 of the electrode head 190 is in registration over the end of the notch 202 that opens into face 198. Thus, window 194 and notch 202 collectively define a portal across the tip assembly 20*d*. It should also be recognized that since windows 191-193 are in fluid communication with window 194 along the underside of the electrode head 190, windows 191-193 are likewise in fluid communication with notch 202. These fluid communication paths form additional portals across the electrode head 190.

The fourth tip assembly 18*d*, like the third tip assembly 18*c*, is used to remove tissue along radial lines that extend perpendicularly from the longitudinal axis of the complementary shaft 14. The fourth tip assembly 18*d*, however, in comparison to the third tip assembly 18*c*, removes only relatively small amounts of tissue at any given moment. This is because, owing to the presence of windows 191-194, the surface area of the head 190 of the electrode 20*d* is relatively small in size. Thus, the tip assembly 18*a* is used to precisely remove relatively small amounts of tissue.

Figure 30:
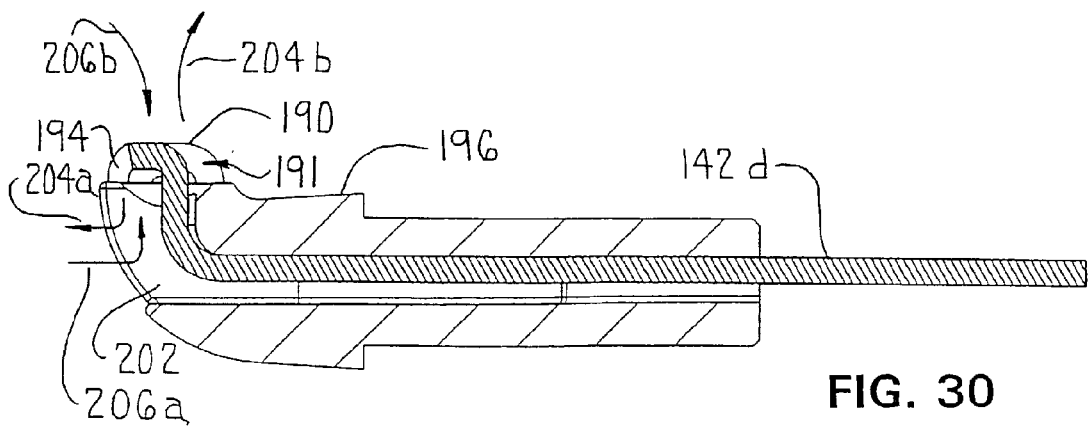
FIG. 30 is a cross sectional view of the fourth tip assembly.

When the tool 10 to which tip assembly 18*d* is actuated, the current flow heats the solution adjacent the electrode head 190. Consequently, convective, liquid-state fluid circulation occurs through the portals as a result of the movement of heated fluid away from electrode head 190 and the flow of cooler replacement fluid towards the electrode head. As depicted in FIG. 30 by arrow 204*a*, some of the heated fluid tends to flow away from the electrode head 190 through the top of the notch 202. As represented by arrow 204*b* another portion of the heated fluid tends to flow outwardly away from the outer surface of the electrode head 190. Some replacement fluid flow, depicted by arrow 206*a*, flows to the electrode head 190 through the lower portion of the notch 202, the portion spaced from the electrode head. Still additional replacement fluid flow, represented by arrow 206*b*, flows toward the outer surface of the electrode head 190.

Eventually, due to the vaporization of the solution, bubbles form on the inner and outer surfaces of the electrode head 190. These bubbles become entrained in the convective fluid flow away from the head through notch 202. Bubbles will also start to form adjacent the side walls 195 of the electrode head 190. These bubbles likewise become entrained in the convective fluid flow away from the tip assembly 20*d*. Thus, this embodiment of the tip assembly, like the other described embodiments, causes the bubbles to flow away from the surgical site so as to minimize the extent to which the bubbles interfere with the surgeon's view of the site.

The electrosurgical tool 10 of this invention is constructed so that the moving components of the switches 29 and 30 that control the actuation of the tool are built into web 108. The web 108 is constructed so that the act of mounting the web 108 to the nose cone 12 seals the border between the web and the nose cone. Thus, the electrosurgical tool 10 of this invention has an on-handle mounted switch assembly for regulating the actuation of the tool that is both economical to install and that does not form paths through which fluid can leak into the handle.

Tool 10 of this invention is also provided with an in-handle identification resistor 105. Depending on the voltage measured across this resistor 105, the complementary control console 22 configures itself to provide the appropriate powered signal to the tool. For example, when the identification resistor 105 indicates that the tool 10 in which the resistor is installed is designed for ear, nose and throat surgery, the control console 22 will configure itself so as to only output a relatively small powered signal to the tool. In some versions of the invention, the maximum power of this low power cutting mode signal may be 50 Watts. If however, the identification resistor 105 indicates that the tool is used for certain orthopedic applications, the control console 22 will configure itself to generate a relatively high powered signal. For example, in some versions of this invention the maximum power of this high power cutting mode signal may be 200 Watts. In still other versions of the invention, the tool emits short bursts of power. When the tool is operated in this mode, it may emit up to 250 Watts of power. As part of this self-configuration, the control console establishes the various power settings for the tool when it is to be operated at less than full power and also when it is to be operated in the coagulation mode.

Figure 9:
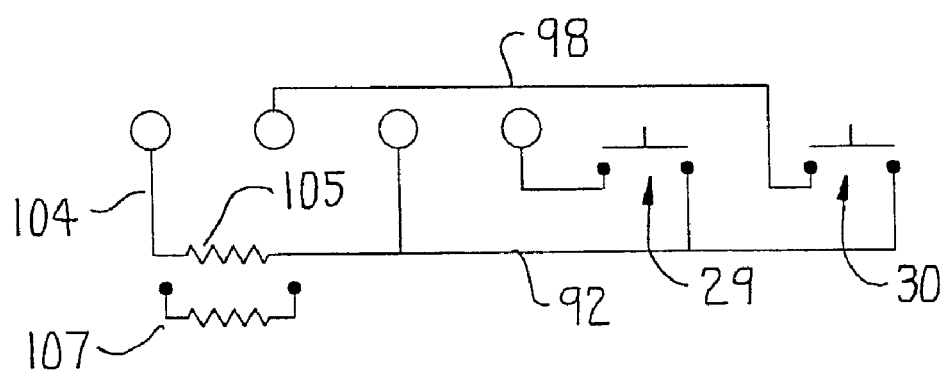
FIG. 9 is a schematic diagram of the electronic circuit integral with the nose cone.

Moreover, in the unlikely event there is a leak of fluid into the nose cone 12, the fluid will most likely flow across conductive trace 104*a* and adjacent trace 92. As represented by a resistor 107 in FIG. 9, this fluid effectively changes the resistance across resistor 105 circuit on printed circuit board 78. The voltage across resistor 105 is always being measured by the voltage measuring circuit 222 internal to the control console 22, even when the tool is actuated. When, due to the insertion of resistor 107 in parallel across resistor 105, the resistance changes, the signal drops out of its normal range the control console circuit 224 recognizes this voltage drop as indication that there is malfunction in the electrosurgical tool 10. This circuit then inhibits the generation of coagulation or ablation causing current so as to prevent persons handling the tool from being shocked. This circuit will also actuate a warning light on the face of the control console (light not illustrated) to indicate that a fault condition has been detected. Also, while the conductive fluid of a leak may flow across one or both of the contact pads 96 or 102 so as to short switch 29 or 30 closed, this malfunction will not result in the tool being unintentionally actuated. Because, as described above, once the leak is detected, the control circuit 224 will have already blocked actuation of the tool 10.

Still another feature of the electrosurgical tool 10 of this invention is that the active electrode is formed out of tantalum. This metal is relatively easy to form into place so as to ensure that the electrode has a desired shape.

Also, the tip assemblies, 18a, 18b, 18c and 18d of this invention are designed so that when the tool is actuated in the cutting mode, the bubbles that are generated are relatively small and flow away from the surgical site. This regulation of bubble formation and flow serves to minimize the extent to which the bubbles both interfere with the surgeon's view of the surgical site and the extent to which they modulate and interrupt the current flow between the tool electrode and the associated shaft. Both these benefits allow the surgeon to focus his/her attentions on performing a procedure with the tool 10 as opposed to dealing with the undesirable consequences of the actuation of the tool.

Moreover, when an electrosurgical tool such as the tool 10 of this invention is operated eschar, dead tissue, sometimes can accumulate on the electrode head. This material can degrade the performance of the tool. However, in the tip assemblies of this invention there is the above-discussed convective flow around the electrode head. This flow serves to remove, to clean, the tissue away from the electrode head so as reduce the effect this tissue has on the operation of the tool.

Figure 32:
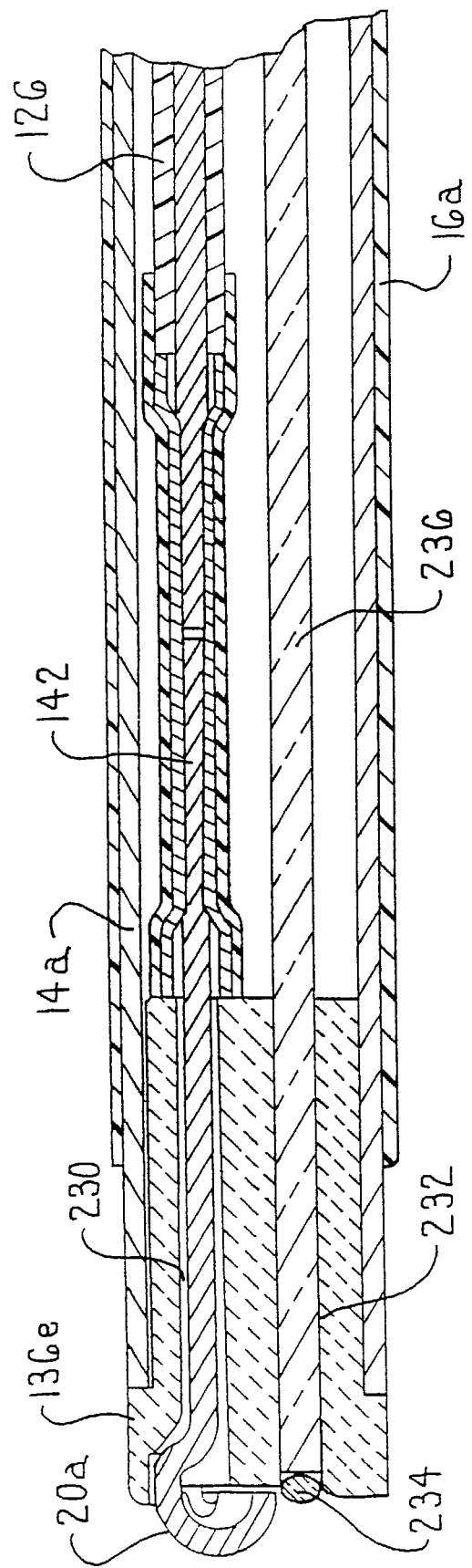
FIG. 32 is a cross sectional view of the distal end of the shaft of an electrosurgical tool illustrating how the tool is fitted with a fiber optic cable.

FIG. 32 depicts the distal end of a shaft 14a of still another version of the electrosurgical tool of this invention. Shaft 14a is formed the same material and performs the same general function as previously described shaft 14. Shaft 14a, is however, larger in diameter than shaft 14. A insulating tube 16a extends around all but the distal end of shaft 14a.

An insulating sleeve 136e is fitted in the open end of shaft 14a. Sleeve 136e is formed to have two parallel, axially extending bores 230 and 232. Electrode 20a is fitted to sleeve 136e so that stem 142 is seated in bore 230. Wire 126 is connected to electrode stem 142 in the manner previously described.

A lens 234 is mounted in the distal end opening of sleeve bore 232. The lens 234 is formed from material such as fused silica glass or other material that has a high degree optical transmisivity for infra-red light, light having a wavelength between 100 nm and 1 mm. A fiber optic cable 236 is seated in bore 232 behind lens 234. Suitable cables that can be employed as fiber optical cable 236 are fluoride or silver halide doped fused silica glass fiber optic cables available from Oxford Electronics of Oxford, England. In some versions of the invention, fiber optic cable has an outer diameter of between 0.1 and 1 mm. Lens 234 is positioned and shaped so as to focus infra-red light waves generated at the surgical site on the distal end, the head end, of the cable 236.

Fiber optic cable 236 is extends out of the proximal end of sleeve 136e and through sleeve 14a. Not illustrated is protective shielding that may extend around the outer surface of cable 236. The fiber optic cable 236 extends through the nose cone 12 to the control console 22. In some versions of the invention, the fiber optic cable 236, or a separate complementary fiber optic cable, is bundled in a version of cable 21 in which the electrical conductors that extend between the nose cone and control console are bundled.

Figure 33:
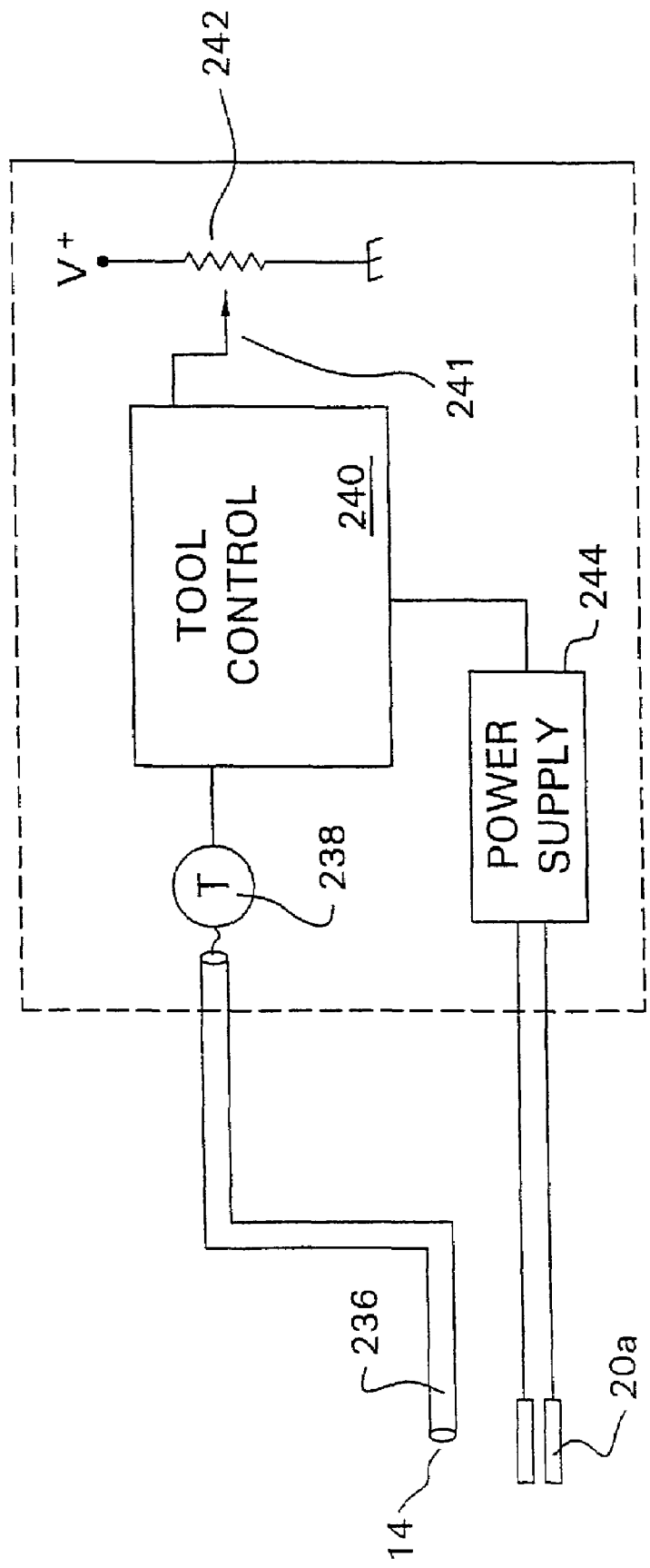
FIG. 33 is a schematic and block diagram of a control console depicting how a signal representative of temperature at the surgical site is obtained and used to regulate the operation of the surgical tool.

FIG. 33 illustrates how the proximal end of fiber optic cable 236 extends to the control console 22a. More specifically, internal to the control console is an infra-red sensitive, photovoltaic transducer 238 to which the light transmitted over fiber optic cable 26 is applied. The signal produced by transducer 238 is applied to tool control circuit 240 as an indication of the temperature of the tissue at the surgical site. In some versions of the invention, a second lens, not illustrated, may be positioned between the proximal end of the fiber optic cable 236 and the transducer 238. This lens is used to either focus or diverge the infra-red light emitted from the proximal end of the cable 236 over the infra-red sensitive surface of the transducer 238.

In the version of the control unit 22 depicted in FIG. 33 a manually-set wiper 241 connected to tool control circuit 240 adjustably applies a fraction of the voltage present across a resistor 242 to the tool controller. This voltage is representative of the temperature desired by the surgeon performing the procedure.

Alternatively, one or both of the buttons 29 and 30 mounted to the nose cone 12 may be used to set the desired temperature. In these versions of the invention, a pulse counter and/or timer circuit is employed to convert the signals generated by the actuation of the button 29 and/or 30 into a command signal indicating the desired temperature setting is to be raised or lowered. For example, in some embodiments of this version of the invention, the surgeon may depress button 29 to indicate that the temperature at the surgical site should be increased. Button 30 is selectively depressed to indicate that the temperature at the surgical site should be decreased.

When the electrosurgical tool of this invention is used to perform a capsulary shrinkage procedure, the appropriate controls are actuated on the control console 22. Tool control circuit 240, in turn, regulates the energization signal produced by a power supply 244 to cause an appropriate voltage to be applied to the active electrode 20a. The active electrode 20a, now in a state in which it generates thermal energy, is applied to the tissue 169 in order to perform the capsulary shrinkage procedure. The heating of the tissue causes the quantity of infra-red energy emitted by the tissue to increase. A portion of this energy is transmitted to lens 234. The infra-red light waves received by lens 234 are focused by the lens are applied to the head end, the distal end of fiber optic cable 236. These light waves are, in turn, forwarded to transducer 238. Transducer 238 thus generates an output signal that varies as a function of the temperature of the tissue 169 forming the surgical site to which the tool is applied.

The output signal produced by transducer 238 is applied to the tool control circuit 240. The tool control circuit 240, based on level of the transducer signal, performs a real time regulation of the power supply 244 to ensure that tool continually heats the tissue to the desired temperature. If the infra-red light detected by transducer 238 rises to a level indicative of a dangerous rise in tissue temperature, tool controller 240 forces the attenuation of the energization signal produced by power supply 244. Thus, the system of this invention regulates the heating of the surgical site 12 by the tool 10 so as to prevent thermally-induced damage of the tissue forming the site.

The electrosurgical tool of this invention monitors the infra-red light generated by the tissue 169 forming the surgical site. The quantity of this light is directly proportional to the temperature of the site. Thus, by monitoring this light, the tool directly monitors the temperature at the surgical site. Moreover, still another feature of the tool of this invention is that the generation of this infra-red light, its collection by the lens 234 and its transmission through fiber optic cable 236 are not affected by the presence of stray electromagnetic waves that may be present due to the actuation of the tool. Thus, the electrosurgical tool of this invention is designed so that, while the active electrode 20a is energized in order to heat the site 12, the temperature of the tissue is simultaneously monitored. This is true for versions of the invention in which an AC energization signal is applied to the electrode 20a. One does not have to apply an energization signal in a pulsed pattern to the active electrode in order monitor site temperature. The tool can thus be energized continually in order to heat large amounts of tissue in a short amount of time so as to cause its capsullary shrinkage.

Collectively, these features mean that the tool of this invention continually applies thermal energy to a surgical site to heat the site to a temperature at which capsulary shrinking occurs at an efficient rate and at which damage to the tissue is avoided.

It should be recognized that the foregoing description is only for the purposes of illustration. Other embodiments of the invention may have features different than what has been described. For example, not all versions of the invention may include the described on-handle switch assembly, the identification resistor, the leak detect traces 92 and 104a or one of the disclosed tip assemblies. Also, in alternative versions of the invention, the number of switches and the function of the switches integral with the switch assembly may vary. For example, in some versions of the invention it may be desirable to provide the switch assembly with switches that can be depressed to establish the power setting of the electrosurgical tool. These switches may be in addition to or in substitution of the switches that regulate the on/off operation of the tool and whether or not the tool is operating in the coagulation mode or the cutting mode. It may also be desirable for some applications to mount a single switch to the nose cone 12.

Moreover, in other versions of the invention, multiple identification resistors may be mounted to the printed circuit board 78. In this configuration, the control circuit internal to the control console 22, would measure the voltages across these individual resistors. Based on these voltages, different settings for the tool can be established. For example, it may be possible to set the control console for one from a first set of maximum power settings when the tool is operated in the coagulation mode and one from a second set of maximum power settings when the tool is operated in the cutting mode.

Alternatively, instead of providing an identification resistor, a digital memory chip may be provided internal to the nose cone 12. This chip would store data that can be used to establish the various power settings of the signals that are applied to the tool 10. These versions of the invention may still contain a resistor. The resistor would serve the leak detect function which resistor 105 performs. Alternatively, the traces on the printed wiring board can be constructed so that if fluid enters the printed wiring board, it establishes a short circuit across the memory chip. In these versions of the invention, the complementary control console is configured to periodically read data from this chip. If, due to the presence of the short circuit, the control console is unable to read this data, a processor internal to the control console interprets this condition as indicating that there is a leak into the nose cone 12. The control console processor, in turn, takes appropriate action to either inhibit the generation of energization signals to the tool and/or actuate the appropriate indicator to inform the surgeon of this fault state.

Moreover, the tip assemblies of this invention may have structures different from what has been described. Other tip assemblies, with through holes in the electrodes and complementary through bores in the insulating sleeves that collectively form contiguous flow pathways may be provided to facilitate to tissue removal in patterns not disclosed. Also, while in the disclosed version of the invention, the corners around the edges of the electrodes 20 are formed at 90°, that may not always be the case. The corners between the surfaces of the electrodes may meet at angles greater or less than 90°. The primary goal in the forming of an electrode is that shaping of its tines so that there will be conductive fluid flow around and/or through the electrode. However, it has been observed that there are current densities that are higher around the sharp corners of the electrodes. These higher current densities result in better ablation of tissue. Accordingly, it is anticipated that other preferred electrodes of this invention will be formed with heads that have sharp corners. Moreover, while in the disclosed version of the invention the portals are oval shaped, circular or rectangular, it should be recognized that this need not always be the case. In other versions of the invention the portals defined by the electrode head and/or insulator sleeve may have different shapes. For example they may even be L-shaped or X-shaped.

Also, the dimensions of the electrodes should be understood to be exemplary and not limiting. Clearly, the windows and portals may be larger or smaller depending on the type of cutting the electrode is designed to perform.

Also, while in FIG. 8, the two traces 92 and 104a that form part of the leak detect circuit are shown as running parallel to each other for a length equal to 72% of the overall length of the printed circuit board 78, that need not always be in the same in each version of this invention. In other versions of the invention, the traces forming the leak detect circuit may run parallel to each other for shorter or longer distances. For example, the traces may run together for a distance only. In still other versions of the invention, the leak detect traces may run together for a length equal to that of the printed circuit board 78 or may even surround the complete perimeter of the printed circuit board. In these latter versions of the invention, the traces would run together for a distance greater than twice the distance around the printed circuit board.

It should similarly be recognized that the self-sealing web 108 may be installed in handpieces integral with surgical tools other than surgical tools. For example, web 108, may be installed in a handpiece that is part of a handpiece with a motor employed to actuate a cutting accessory. Alternatively, the web 108 may be installed in handpiece that is part of surgical laser or surgical ultrasonic tool.

Moreover, while the described version of the electrosurgical tool 10 of this invention is a bipolar tool, alternative monopolar versions of this tool can be provided. A monopolar electrosurgical tool has a single electrode. When electrosurgery with this type of tool is performed, the patient is externally grounded.

Furthermore, it may not be necessary to extend the fiber optic cable 236 of this invention to the complementary control console 22 to which the eleoctrosurgical tool is connected. In some versions of this invention, an infra-red transducer identical or similar to transducer 238 may be mounted in the nose cone 12 of the electrosurgical tool. In these versions of the invention, the output signal produced by the transducer is transmitted to the tool controller 222 in the control console 22 over electrical conductors in the cable 21. An advantage of this version of the invention is that the need to extend the fiber optic cable to the control console is eliminated. In these versions of the invention it should be realized that the transducer may be mounted to a circuit board internal to the nose cone 12 that is separate and sealed from the circuit board 78 forming the switch assembly.

Therefore, it is the object of the appended claims to cover all such variations and modifications that come within the spirit and scope of this invention.

What is claimed is:

1. An electrosurgical tool having a proximal end and a distal end spaced therefrom, said tool comprising:
   a handle;
   an electrode arrangement extending from said handle and including an active electrode disposed at said distal end of said tool, said electrode defining a tissue-contacting end which heats tissue upon electrical actuation of said electrode and causes the tissue to emit infra-red light;
   an infra-red light transmitting member having an infra-red light output portion disposed proximally of said distal end of said tool and an infra-red light input portion disposed at said distal end of said tool adjacent said tissue-contacting end of said electrode, said input portion including a distal end surface which captures infra-red light generated exteriorly of said tool by tissue heated by said electrode and transmits such infra-red light proximally to said output portion; and
   a control console including an infra-red sensitive transducer connected to said output portion of said light transmitting member and generating an output indicative of a temperature of tissue heated by said electrode, a power source for providing electrical energy to said electrode, and a control circuit connected to said transducer and configured to regulate an energization signal of said power source based upon said output of said transducer to control an amount of thermal energy generated by said electrode.

2. The tool of claim 1, wherein said distal end surface of said input portion defines a terminal end of said light transmitting member.

3. The tool of claim 2, wherein said input portion includes a lens mounted at said distal end of said tool adjacent said tissue-contacting end of said electrode and defining said distal end surface of said input portion, said light transmitting member including a fiber-optic cable defining an infra-red light receiving distal end defining part of said input portion and an infra-red light emitting proximal end defining said output portion, said lens being disposed to focus infra-red light generated by heated tissue onto said distal end of said fiberoptic cable for transmission to said proximal end of said fiberoptic cable.

4. The tool of claim 1, further including an elongate shaft mounted on and extending distally from said handle, said electrode being disposed interiorly of said shaft and projecting outwardly from a distal end thereof.

5. The tool of claim 4, wherein said light transmitting member is disposed interiorly of said shaft adjacent said electrode.

6. The tool of claim 1, further including an elongate and generally tubular shaft mounted on and projecting distally from a distal end portion of said handle, said electrode arrangement being disposed within said shaft and said shaft defining a return electrode thereon at a distal end thereof adjacent said active electrode.

7. The tool of claim 6, wherein said shaft is constructed of electrically-conductive material covered by an insulating material, an exposed portion of said shaft defining said return electrode.

8. The tool of claim 1, wherein said control circuit regulates an energization signal of said power source based upon said output of said transducer, without requiring the projection of light upon tissue at the surgical site.

9. A bipolar electrosurgical tool comprising:
   a handle;
   an elongate shaft connected to said handle and having a proximal end disposed adjacent said handle and a distal end spaced from said proximal end, said shaft being tubular so as to define an interior channel therein;
   an electrode arrangement disposed within said channel of said shaft and including an active electrode projecting from said distal end thereof and defining thereon a tissue-contacting portion which when electrically actuated heats targeted tissue to a predetermined temperature, said shaft being constructed of electrically conductive material and defining a return electrode disposed adjacent said active electrode;
   an elongate, infra-red light transmitting arrangement including a light-transmitting element and an infra-red light receiving lens disposed at said distal end of said shaft adjacent said tissue-contacting portion of said active electrode, said light transmitting element including an infra-red light input end disposed closely adjacent said lens and an infra-red light output end disposed proximally of said lens, said lens being disposed to receive infra-red light waves directly from tissue heated by said active electrode and to focus such infra-red light waves onto said input end of said light transmitting element for transmission to said output end thereof; and
   a control console including a control circuit having an input associated with said output end of said light transmitting element and an output associated with said electrode arrangement, said control circuit being configured to regulate an energization signal of a power source associated with said electrode arrangement based upon infra-red light waves generated by tissue heated by said active electrode.

10. The tool of claim 9, wherein said light transmitting element is disposed within said channel of said shaft, said distal end of said shaft opening outwardly and mounting therein an insulating sleeve-shaped member through which said input end of said light transmitting element and said active electrode extend, said lens being mounted within said sleeve-shaped member distally of said input end of said light transmitting element.

11. The tool of claim 10, wherein said sleeve-shaped member defines a pair of passages therein, said input end of said light transmitting element and said lens being disposed in one of said passages and said active electrode being disposed in the other of said passages.

12. The tool of claim 9, wherein said control console includes an infra-red sensitive transducer interposed between said output end of said light transmitting element and said input of said control circuit, said transducer generating a signal for said control circuit indicative of a temperature of the tissue heated by said active electrode at the surgical site.

13. The tool of claim 9, wherein said light transmitting element transmits infra-red light waves generated exteriorly of said tool by heated tissue at the surgical site in a direction from said input end to said output end, and said control circuit regulates an energization signal of a power source associated with said electrode arrangement based upon infra-red light waves generated by tissue heated by said active electrode, without requiring the projection of light waves upon the tissue at the surgical site.

14. The tool of claim 9, further including an insulating layer disposed about said shaft, a portion of said shaft projecting distally beyond a terminal end of said insulating layer and defining said return electrode.

15. An electrosurgical tool comprising:
   a handle;
   an electrode arrangement mounted on said handle and including an electrode disposed at a distal end of said tool, said electrode defining a tissue-contacting portion which heats tissue to a predetermined temperature such that the tissue emits infra-red light;
   an infra-red light transmitting arrangement including a light transmitting member having an infra-red light input end and an infra-red light output end disposed proximally of said input end, and an infra-red light input member disposed distally of said input end of said light transmitting member at said distal end of said tool adjacent said tissue-contacting portion of said electrode, said input member being disposed and configured to collect infra-red light generated by tissue heated by said electrode at the surgical site and directly transmit such infra-red light from the surgical site to said input end of said light transmitting member; and
   a control unit having a control circuit including an infra-red light input coupled to said output end of said light transmitting member and an infra-red light limited electrical-energy output coupled to said electrode, said control circuit monitoring infra-red light emitted by the tissue at the surgical site and controlling an energization signal provided to said electrode by said electrical-energy output based upon the amount of infra-red light emitted by the tissue.

16. The tool of claim 15, wherein said input member defines a terminal distal end of said light transmitting arrangement.

17. The tool of claim 15, further including an elongate shaft mounted on and projecting distally from said handle, said shaft defining a hollow interior in which said electrode arrangement is disposed.

18. The tool of claim 17, wherein said electrode is a first active electrode, and said shaft has a portion constructed of electrically-conductive material which defines a second return electrode disposed at said distal end of said tool adjacent said active electrode.

19. A method of regulating temperature at a surgical site with an electrosurgical tool and a tool control unit, said method comprising the steps of:
   actuating a tool control unit to apply electrical energy to an electrosurgical tool;
   generating thermal energy with the electrosurgical tool in response to the application of electrical energy thereto;
   locating the electrosurgical tool adjacent a surgical site;
   applying thermal energy to tissue at the surgical site with the electrosurgical tool to heat the tissue and cause same to generate infra-red light;
   capturing the infra-red light generated by the heated tissue at the surgical site with the electrosurgical tool and thereafter transmitting the infra-red light generated by the heated tissue at the surgical site away from the surgical site to the tool control unit;
   generating an output signal with the tool control unit representative of temperature at the surgical site based upon the transmitted infra-red light; and
   regulating the electrical energy applied by the tool control unit to the electrosurgical tool based upon the output signal.

20. A method of regulating temperature at a surgical site with an electrosurgical tool and a tool control unit, wherein the electrosurgical tool includes a fiber optic cable and a lens positioned at a distal end thereof, said method comprising the steps of:
   actuating a tool control unit to apply electrical energy to an electrosurgical tool;
   generating thermal energy with the electrosurgical tool in response to the application of electrical energy thereto;
   locating the electrosurgical tool adjacent a surgical site;
   applying thermal energy to tissue at the surgical site with the electrosurgical tool to heat the tissue and cause same to generate infra-red light;
   with the lens, capturing the infra-red light generated by the heated tissue at the surgical site and focusing the infra-red light generated by the heated tissue at the surgical site toward the distal end of the fiber optic cable;
   transmitting the focused infra-red light along the fiber optic cable away from the surgical site to the tool control unit;
   generating an output signal with the tool control unit representative of temperature at the surgical site based upon the transmitted infr-ared light; and
   regulating the electrical energy applied by the tool control unit to the electrosurgical tool based upon the output signal.

21. The method of claim 20, further including reducing electrical energy applied to the electrosurgical tool by the tool control unit in response to a change in the output signal.

* * * * *